United States Patent
Berger

(10) Patent No.: US 12,083,192 B2
(45) Date of Patent: Sep. 10, 2024

(54) METHODS FOR TREATMENT OF PATIENTS WITH MYELODYSPLASTIC SYNDROMES

(71) Applicant: Actinium Pharmaceuticals, Inc., New York, NY (US)

(72) Inventor: Mark Berger, New York, NY (US)

(73) Assignee: Actinium Pharmaceuticals, Inc., New York, NY (US)

( * ) Notice: Subject to any disclaimer, the term of this patent is extended or adjusted under 35 U.S.C. 154(b) by 706 days.

(21) Appl. No.: 16/766,009

(22) PCT Filed: Dec. 4, 2018

(86) PCT No.: PCT/US2018/063795
§ 371 (c)(1),
(2) Date: May 21, 2020

(87) PCT Pub. No.: WO2019/113031
PCT Pub. Date: Jun. 13, 2019

(65) Prior Publication Data
US 2020/0276339 A1    Sep. 3, 2020

Related U.S. Application Data

(60) Provisional application No. 62/594,259, filed on Dec. 4, 2017.

(51) Int. Cl.
| | | |
|---|---|---|
| *A61K 51/10* | (2006.01) | |
| *A61K 31/10* | (2006.01) | |
| *A61K 31/198* | (2006.01) | |
| *A61K 31/675* | (2006.01) | |
| *A61K 31/7076* | (2006.01) | |
| *A61P 35/00* | (2006.01) | |
| *A61P 35/02* | (2006.01) | |
| *C07K 16/28* | (2006.01) | |
| *C12Q 1/6886* | (2018.01) | |
| *A61K 39/00* | (2006.01) | |

(52) U.S. Cl.
CPC .......... *A61K 51/1033* (2013.01); *A61K 31/10* (2013.01); *A61K 31/198* (2013.01); *A61K 31/675* (2013.01); *A61K 31/7076* (2013.01); *A61K 51/1069* (2013.01); *A61P 35/00* (2018.01); *A61P 35/02* (2018.01); *C07K 16/2803* (2013.01); *C12Q 1/6886* (2013.01); *A61K 2039/505* (2013.01); *C07K 2317/24* (2013.01); *C12Q 2600/156* (2013.01)

(58) Field of Classification Search
CPC .. A61K 51/1033; A61K 31/10; A61K 31/198; A61K 31/675; A61K 31/7076; A61K 51/1069; A61K 2039/505; A61P 35/00; A61P 35/02; C07K 16/2803; C07K 2317/24; C12Q 1/6886; C12Q 2600/156; G01N 2333/4748
See application file for complete search history.

(56) References Cited

U.S. PATENT DOCUMENTS

| | | |
|---|---|---|
| 5,730,982 A | 3/1998 | Scheinberg |
| 2017/0326259 A1 | 11/2017 | Dave |
| 2018/0127831 A1 | 5/2018 | Hebert et al. |
| 2018/0296708 A1 | 10/2018 | Dave |
| 2020/0121815 A1 | 4/2020 | Seth et al. |

FOREIGN PATENT DOCUMENTS

WO    WO-2018200562 A1 *  11/2018  ............. A61K 35/17

OTHER PUBLICATIONS

Rucker et al., Blood, Mar. 1, 2012, vol. 119, No. 9, 2114-2121. (Year: 2012).*
Niu et al., Biomaterials 167 (2018) 132-142 (Year: 2018).*
Sutherland, MSK et al., SGN-CD33A: A Novel CD33-Targeting Antibody-Drug Conjugate Utilizing a Pyrrolobenzodiazepine Dimer is Active in Models of Drug-resistant AML. Blood. Aug. 22, 2013, vol. 22, No. 8, pp. 1455-1463.
Stirewalt, DL et al., Fl T3, RAS, and TP53 mutations in elderly patients with acute myeloid leukemia. Blood. Jun. 1, 2001, vol. 97, No. 11, pp. 3589-3595.
Burke, JM et al., Cytoreduction with iodine-131-anti-CD33 antibodies before bone marrow transplantation for advanced myeloid leukemias. Bone Marrow Transplantation. Sep. 2003, vol. 32, No. 6, pp. 549-556.
Jurcic, JG et al., Phase I Trial of Targeted Alpha-Particle Therapy with Actinium-225 (Ac)-Lintuzumab and Low-Dose Cytarabine (LDAC) in Patients Age 60 or Older with Untreated Acute Myeloid Leukemia (AML). Blood. 2016, vol. 128, No. 22, p. 4050.
Jilani, I. et al., Differences in CD33 Intensity Between Various Myeloid Neoplasms, Am J Clin Pathol 2002;118:560-566.
Sanford, D. et al., CD33 is frequently expressed in cases of myelodysplastic syndrome and chronic myelomonocytic leukemia with elevated blast count, Leuk Lymphoma. Aug. 2016 ; 57(8):1965-1968.
Deeg, H. et al., Five group cytogenetic risk classification, monosomal karyotype, and outcome after hematopoietic cell transplantation for MDS or acute leukemia evolving from MDS, Blood, Aug. 16, 2012 vol. 120, No. 7, 1398-1408.

(Continued)

Primary Examiner — Robert S Cabral
(74) Attorney, Agent, or Firm — Dentons Cohen & Grigsby P.C.; Michael E. Dukes

(57) ABSTRACT

Methods for treating a proliferative disease in hematologic malignancy in a subject having a complex karyotype by administering an effective amount of an immunotherapy which includes a targeting agent for an epitope of CD33. The proliferative disease may be a hematological disease or disorder such as multiple myeloma, acute myeloid leukemia, myelodysplastic syndrome, and myeloproliferative neoplasm. The effective amount of the anti-CD33 targeting agent may be an amount sufficient to induce myeloconditioning or an amount to induce myeloablation. The methods may further include transplanting allogeneic stem cells to the patient after administration of the anti-CD33 targeting agent.

18 Claims, 1 Drawing Sheet
Specification includes a Sequence Listing.

(56) References Cited

OTHER PUBLICATIONS

Getta, B. et al., Allogeneic Hematopoietic Stem Cell Transplantation Is Underutilized in Older Patients with Myelodysplastic Syndromes, Biol Blood Marrow Transplant 23 (2017) 1078-1086.
Greensberg, P. et al., Revised International Prognostic Scoring System for Myelodysplastic Syndromes, Blood, Sep. 20, 2012 vol. 120, No. 12, 2454-2465.
Prokocimer, H. et al., Dysfunctional diversity of p53 proteins in adult acute myeloid leukemia: projections on diagnostic workup and therapy, Blood, Aug. 10, 2017 + vol. 130, No. 6, 699-712.
Podoltsev et al., "Selecting initial treatment of acute myeloid leukaemia in older adults", Blood Reviews, 31(2):43-62 (Oct. 8, 2016).
Jen, "Actinium Pharmaceuticals—Two Novel Acute Myeloid Leukemia (AML) Radiotherapeutics in Development Supported by Strong Balance Sheet", Laidlaw & Company, pp. 1-20 (Feb. 26, 2015).
Burke et al., "Antibody Therapy in Acute Myeloid Leukemia: Current Status and Future Directions", Clinical Lymphoma, 2(Supp. 01):S12-S18 (Mar. 2002).
Jurcic et al., "Targeted Alpha-Particle Immunotherapy for Acute Myeloid Leukemia", Educational Book, vol. 34, pp. e126-e131 (2014).
Jurcic et al., "Phase I trial of the targeted alpha-particle nano-generator actinium-225 (225 Ac-lintuzumab) (anti-CD33; HuM195) in acute myeloid leukemia (AML)", Journal of Clinical Oncology, 29(15):6516 (May 20, 2011).
Jurcic, "Targeted Alpha-Particle Immunotherapy with Bismuth-213 and Actinium-225 for Acute Myeloid Leukemia", Journal of Postgraduate Medicine Education and Research, vol. 47, pp. 14-17 (Jan. 15, 2013).
Jurcic et al., Phase I trial of [alpha]-particle therapy with actinium-225 (225 Ac)-lintuzumab) (anti-CD33) and low-dose cytarabine (LDAC) in older patients with untreated acute myeloid leukemia (AML), Journal of Clinical Oncology, 5 pages (May 20, 2015).
Walter, "Investigational CD33-targeted therapeutics for acute myeloid leukemia", Expert Opinion on Investigational Drugs, 27(4):339-348 (Jan. 1, 2018).
Masarova et al., "Harnessing the Immune System Against Leukemia: Monoclonal Antibodies and Checkpoint Strategies for AML", Retinal Degenerative Diseases: Advances in Experimental Medicine and Biology, vol. 995, pp. 73-95 (Jan. 1, 2017).
Montalban-Bravo et al., "Novel drugs for older patients with acute myeloid leukemia", Leukemia, 29(4):760-769 (Aug. 21, 2014).
Anonymous, "History of Changes for Study:NCT02575963, Lintuzumab-Ac225 in Older Acute Myeloid Leukemia (AML) Patients", pp. 1-7 (Oct. 3, 2017).
Anonymous, "Lintuzumab-Ac225 in Older Acute Myeloid Leukemia (AML) Patients", pp. 1-9 (Nov. 20, 2020).

* cited by examiner

SEQ ID NO: 1

Extracellular domain

MPLLLLLPLLWAGALAMDPNFWLQVQESVTVQEGLCVLVPCTFFHPIPYY

DKNSPVHGYWFREGAIISRDSPVATNKLDQEVQEETQGRFRLLGDPSRNN

CSLSIVDARRRDNGSYFFRMERGSTKYSYKSPQLSVHVTDLTHRPKILIP

GTLEPGHSKNLTCSVSWACEQGTPPIFSWLSAAPTSLGPRTTHSSVLIIT

PRPQDHGTNLTCQVKFAGAGVTTERTIQLNVTYVPQNPTTGIFPGDSGK

QETRAGVVII GAIGGAGVTALLALCLCLIFFIV KTHRRKAARTAVGRNDTH

PTTGSASPKHQKKSKLHGPTETSSCSGAAPTVEMDEELHYASLNFHGMNP

SKDTSTEYSEVRTQ

Intracellular domain

SEQUENCE LISTING

```
<160> NUMBER OF SEQ ID NOS: 1

<210> SEQ ID NO 1
<211> LENGTH: 364
<212> TYPE: PRT
<213> ORGANISM: Homo sapiens

<400> SEQUENCE: 1

Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
                20                  25                  30

Glu Gly Leu Cys Val Leu Val Pro Cys Thr Phe Phe His Pro Ile Pro
            35                  40                  45

Tyr Tyr Asp Lys Asn Ser Pro Val His Gly Tyr Trp Phe Arg Glu Gly
        50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
```

```
                      210                 215                 220
Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360
```

METHODS FOR TREATMENT OF PATIENTS WITH MYELODYSPLASTIC SYNDROMES

CROSS-REFERENCE TO RELATED APPLICATIONS

The present application is a 371 national stage filing of PCT Patent Application No. PCT/US2018/063795 filed Dec. 4, 2018, which claims the benefit under 35 U.S.C. § 119(e) of prior U.S. Provisional Application Ser. No. 62/594,259, filed Dec. 4, 2017, the entire content of both of which is incorporated herein.

SEQUENCE LISTING

This application contains a Sequence Listing in computer readable form which is incorporated herein by reference. The sequence listing text file "SequenceListing17048_ST25" submitted via EFS in compliance with 37 CFR § 1.52(e)(5) and Rule 13ter.1(a) is identical to the sequence listing forming part of this international application.

FIELD OF THE INVENTION

The present invention relates to targeted conditioning with anti-CD33 immunotherapy in patients with hematological cancers or disorders, and in particular to methods for treating myelodysplastic syndromes in patients who present with poor or very poor cytogenetic groups by administration of an anti-CD33 targeting agent, such as an antibody, antibody fragment, Fab fragment, or aptamer.

BACKGROUND OF THE INVENTION

Myelodysplastic syndromes (MDS), formerly known as pre-leukemia, are clonal disorders of human stem cells characterized by ineffective hematopoiesis leading to a drop in red blood cells, platelets, and normal white blood cells (cytopenias, mainly anemia). It is thought to arise from a clonal process affecting a single hematopoietic progenitor cell. It has been suggested that these cells of origin have acquired multiple mutations resulting in the morphologic and functional aberrations which define the disease. For example, erythroid cell dysplasia is observed in 50% of early stage MDS. The syndromes may arise de novo, or secondarily after treatment with chemotherapy and/or radiation therapy for other diseases. Secondary MDS usually has a poorer prognosis than de novo MDS.

The disease is characterized by progressive cytopenias leading to complications of bone marrow failure, including fatigue, infection, anemia, and bleeding. Most patients become dependent on blood and/or platelet transfusions. The International Prognostic Scoring System-Revised (IPSS-R) is used to assess prognosis of MDS (Greenberg, et al., "Revised International Prognostic Scoring System for Myelodysplastic Syndromes," 2012, Blood, vol. 120(12): 2454-2465). The IPSS-R uses several variables to determine a risk score, which include cytogenetic risk groups, marrow blast percentage, and depth of cytopenias (hemoglobin, platelet, and absolute neutrophil levels). IPSS-R scores separate patients into five categories of risk, ranging from very low (median survival 8.8 years) to very high (0.8 years), which are used to determine treatment.

MDS patients, especially those in the IPSS-R high and very high-risk categories (poor and very poor prognosis), may progress to acute myeloid leukemia (AML), which is often refractory to standard therapies. Multiple myeloma (MM) is also found among patients with MDS, especially in older patients. Moreover, certain cytogenetic abnormalities identified by fluorescence in situ hybridization or karyotypic analysis carry prognostic significance for patients with MDS and impact treatment planning. Complex cytogenetics, defined as 3 or >3 cytogenetic abnormalities in one clone of cells, are in a "poor" or "very poor" cytogenetic prognostic subgroup in the IPSS-R, respectively. These patients automatically fall into the intermediate or higher risk categories for the IPSS-R.

Advances in the treatment of MDS based on the heterogeneous biology of this clonal disease have led to the FDA approval of the hypomethylating agents azacytidine and decitabine, which have been shown to improve cytopenias, quality of life and, in some cases, prolong survival. However, allogeneic bone marrow or hematopoietic stem cell transplantation (HSCT) is the only curative option for patients with MDS. Early referral for HSCT is considered the standard of care for eligible patients with higher risk MDS.

Despite its curative potential, transplantation is performed relatively infrequently in MDS, as demonstrated in a publication from the Memorial Sloan Kettering Cancer Center, where, when 362 unselected patients were evaluated, only 33% underwent HSCT at a median of 7 months from diagnosis. In multivariate analysis, age ≥65 (p=0.021), presence of ≥2 comorbidities (p=0.018), and <5% blasts (overall p=0.011) were associated with a lower likelihood of undergoing transplantation (Getta, et al., "Allogeneic Hematopoietic Stem Cell Transplantation is Underutilized in Older Patients with Myelodysplastic Syndromes," 2017, Biol Blood Marrow Transplant, 23:1078-1086). Thus, although transplant is widely acknowledged to have curative potential in MDS, the combination of significant transplant-related toxicities and high failure rates in patients with advanced disease leave important opportunities for improvement. Other barriers to HSCT include older age, poor performance status, and/or donor availability. Finally, patients with active disease are generally not referred for transplant as it is clear that residual disease burden results in inferior outcomes. Thus, conditioning therapies that are more effective in pre-transplant disease eradication are needed.

This issue is especially important in patients with high IPSS-R scores, who have high rates of relapse after allogeneic transplantation. Of note, even younger "fit" patients who are treated with myeloablative conditioning strategies for MDS experience high rates of relapse when they have active disease at the time of conditioning.

A number of efforts have been made to elucidate which group of patients would benefit from non-transplant approaches with hypomethylating agents versus allogeneic HSCT. Based on patient age and IPSS risk stratification, a recent international collaborative decision analysis for de novo MDS patients aged 60 to 70 years demonstrated that for low/intermediate-1 IPSS scores, non-transplantation approaches are preferred. For patients with intermediate-2/high IPSS scores, allogeneic transplantation with reduced intensity conditioning regimens offers quality adjusted overall survival benefit. Since myeloablative conditioning is generally reserved for younger patients, reduced intensity conditioning allogeneic HSCT has been steadily increasing in the older patients with higher risk MDS. However, the limitation of reduced intensity conditioning is that it is not intense enough to eradicate high risk MDS, leading to an increase in relapse compared to low risk MDS patients who receive reduced intensity conditioning prior to allogeneic HSCT (see for example Deeg, et al, "Five-group cytogenetic risk classification, monosomal karyotype, and outcome after hematopoietic cell transplantation for MDS or acute leukemia evolving from MDS," 2012, Blood, vol. 120(7):1398-1408).

It is unclear which regimen would be the most suitable for patients of all ages with MDS since younger patients, or those without comorbidities, receive myeloablative conditioning regimens based on their clinical tolerability. Patients who are older and less fit often receive reduced intensity conditioning regimens, while younger, fit patients receive myeloablative conditioning. That is, in preparation for HSCT, agents may be administered to condition, lymphodeplete, or ablate the stem cells and/or malignant cells. Current non-targeted conditioning methods, which include, for example, irradiation (e.g., total body irradiation) and DNA alkylating/modifying agents, are highly toxic to multiple organ systems, hematopoietic and non-hematopoietic cells, and the hematopoietic microenvironment. These harsh conditioning regimens effectively kill the patient's immune and niche cells and adversely affect multiple organ systems, frequently leading to life-threatening complications.

Three randomized studies have been performed that compare myeloablative conditioning vs reduced intensity conditioning and include AML and MDS. These studies demonstrated mixed results. The first of these 3 studies used higher or lower total body irradiation, respectively, in the conditioning regimens and did not show significance between regimens. A study comparing the chemotherapeutic agents Bu/Cy (myeloablative conditioning; busulfan, 16 mg/kg orally or 12.8 mg/kg intravenously, plus cycoposphosphamide, 120 mg/kg) vs Flu/Bu2 (reduced intensity conditioning; fludarabine, 120-180 mg/nm, plus busulfan, ≤8 mg/kg orally or 6.4 mg/kg intravenously) demonstrated relapse-free survival and overall survival rates that were similar. Both trials had accrual issues which were mitigated by The Bone Marrow Transplant Clinical Trials Network (BMT-CTN) study by allowing for more flexibility of regimens through use of 3 myeloablative conditioning regimens (Flu/Bu4: Fludarabine, 120-180 mg/m$^2$, plus busulfan. 16 mg/kg orally or 12.8 mg/kg intravenously; Bu/Cy; or TBI/Cy: Cyclophosphamide, 120 mg/kg, plus total-body irradiation, 1,200-1,420 cGy) vs 2 reduced intensity conditioning regimens (Flu/Bu2 or Flu/Mel: Cyclophosphamide, 120 mg/kg, plus total-body irradiation, 1,200-1,420 cGy), leading to more rapid accrual (272 patients<3 years).

While the relapse-free survival and overall survival was higher with myeloablative conditioning, the superior trend in overall survival did not reach statistical difference. Furthermore, when a sub-analysis was performed on the 54 patients with MDS, there was no difference in survival between myeloablative conditioning and reduced intensity conditioning. There were not enough patients with Flu/Mel to address superiority of one reduced intensity conditioning regimen over the other.

Recently, the Center for International Blood and Marrow Transplant research (CIBMTR) analyzed the optimal conditioning intensity for AML and MDS by studying patients undergoing non-irradiation containing regimens transplanted between 2009 and 2014. Patients had a median age of 58 years, with both AML (n=1258) and MDS (n=951) patients included. High intensity regimens of Bu4/Cy had a 3-year relapse-free survival (44%) comparable with high intensity Flu/Bu4 (44%), reduced intensity Flu/Mel (52%), and Flu/Mel+anti-thymocyte globulin (ATG; 31%). Reduced intensity Flu/Bu2 with or without ATG, resulted in lower relapse-free survival. In terms of reduced intensity regimens, relapse-free survival with Flu/Mel is superior to the relapse-free survival with Flu/Bu2 and Flu/Bu2+ATG. The incidence of relapse was lower at 3 years with Flu/Mel (22%) that with Flu/Bu2±ATG (46% and 56%, respectively). This higher relapse rate resulted in lower relapse free survival for Flu/Bu2. These data suggest that the lower relapse rate with Flu/Mel yields relapse-free survival comparable to higher intensity regimens. 80% of the Flu/Mel patients received melphalan at a dose of 140 mg/m$^2$, and the remaining received dose of 100 mg/m$^2$.

In a recent retrospective single center analysis of 156 patients with AML between 2005 and 2014, Flu/Mel provided non-inferior disease control compared to myeloablative Bu/Cy, which is given in younger fit patients. Flu/Mel was also safely combined with alemtuzumab to reduce acute and chronic graft-versus-host disease, without affecting long term outcomes. Furthermore, a large nationwide, retrospective study comparing 3 regimens in 1607 patients >50 years, transplanted in Japan between 2007 and 2014, suggested that Flu/Mel 140 mg/m$^2$ may be associated with better overall survival in patients with high risk AML and MDS, compared to Flu/Bu4 or Flu/Bu2. While Flu/Bu2 has an advantage with lower treatment related mortality and is better tolerated by older patients, the higher relapse in these studies outweighs any potential advantage over a Flu/Mel regimen. The advantages of Flu/Mel based on the above studies includes one single regimen applicable to all ages, and potential equivalency to myeloablative regimens, with better tolerability.

Based on the recently revised international prognostic scoring system (IPSS-R), the European Society for Blood and Marrow Transplantation recently analyzed their database of 903 patients undergoing HSCT and demonstrated that poor and very poor risk cytogenetics were strong predictors of adverse patient outcomes. Furthermore, when allogeneic HSCT was performed in those with TP53 mutations, which are frequently detected in patients with therapy-related acute myeloid leukemia (AML) or AML with complex karyotype (AML-CK), the overall survival at 1 year was only 17% in those patients with poor performance status, multiple co-morbidities, or who were beyond their first complete response. This study also found that myeloablative doses of busulfan-based conditioning at >20,000 uMol/min were associated with better progression-free survival compared to lower doses of busulfan. This supports the rationale for myeloablative or more intense conditioning prior to transplant, given that relapse is the major limitation for HSCT in high risk MDS and optimal disease control is required. New approaches to overcome the toxicity of the higher dose regimens known in the prior art are needed to overcome the higher treatment related toxicity associated with them, while the current reduced intensity conditioning regimens have the drawback of relapse. This also highlights the need for novel therapies, including improvements in HSCT in this high-risk poor prognostic group of patients.

Thus, there exists a need for improved methods for treating cancers, such as myelodysplastic syndromes, in patients in a "poor" or "very poor" cytogenetic prognostic subgroup according to the IPSS-R. Moreover, there exists a need for improved methods for myeloconditioning and myeloablation prior to HSCT in the treatment of myelodysplastic syndromes, particularly in patients in these cytogenetic prognostic subgroups.

SUMMARY OF THE INVENTION

The present invention is related to improved methods for treating hematological diseases or disorders. The methods generally include administering to the patient an effective amount of a targeting agent which specifically binds to an epitope of CD33 (anti-CD33 targeting agent, antibody fragment, peptide, Fab fragment, aptamer, etc). The effective amount of the anti-CD33 targeting agent may be a maximum tolerated dose (MTD) of the targeting agent, or may be an amount sufficient to induce myeloconditioning or myeloablation. Such treatment may be an effective precursor to transplantation with allogeneic stem cells, and may provide improved treatment outcomes for a category of patients having poor outcomes with standard prior art therapies (i.e., radiation and/or chemotherapy).

According to certain aspects of the present invention, the proliferative disorder may be a hematological disease or disorder such as multiple myeloma, acute myeloid leukemia, myelodysplastic syndrome, and/or myeloproliferative neoplasm. Moreover, the proliferative disorder may be associated with cells expressing CD33.

According to certain aspects of the present invention, the hematological disease or disorder may be a myelodysplastic syndrome in patients having a p53 mutation, or in patients who are in the poor or very poor cytogenetic prognostic groups, as defined by the IPSS-R.

According to certain aspects of the present invention, the anti-CD33 targeting agent may comprise a humanized antibody against CD33, such as lintuzumab (HuM195), gemtuzumab, or vadastuximab.

According to certain aspects of the present invention, the anti-CD33 targeting agent may comprise a radioisotope, such as: $^{131}$I, $^{125}$I, $^{123}$I, $^{90}$Y, $^{177}$Lu, $^{186}$Re, $^{188}$Re, $^{89}$Sr, $^{153}$Sm, $^{32}$P, $^{225}$Ac, $^{213}$Bi, $^{213}$Po, $^{211}$At, $^{212}$Bi, $^{213}$Bi, $^{223}$Ra, $^{227}$Th, $^{149}$Tb, $^{137}$Cs, $^{212}$Pb and $^{103}$Pd.

According to certain aspects of the present invention, when the anti-CD33 targeting agent comprises a radioisotope, the methods may further comprise transplanting allogeneic stem cells to the subject after administration of the anti-CD33 targeting agent at a time when a radiation dose from the anti-CD33 targeting agent is not harmful to the transplanted cells, such as 8 to 20 days after the administration of the anti-CD33 targeting agent, or even 10 to 16 days after administration of the anti-CD33 targeting agent.

According to certain aspects of the present invention, the effective amount of the anti-CD33 targeting agent may comprise a dose of less than 16 mg/kg body weight of the subject, less than 10 mg/kg body weight of the subject, or even less than 6 mg/kg body weight of the subject.

According to certain aspects of the present invention, the anti-CD33 targeting agent comprises lintuzumab at least partially labelled with $^{131}$I or $^{225}$Ac. Thus, the anti-CD33 targeting agent may comprise a labelled fraction of the anti-CD33 targeting agent, such as $^{131}$I-lintuzumab or $^{225}$Ac-lintuzumab, and an unlabeled fraction of the ant-CD33 targeting agent.

According to certain aspects of the present invention, the effective amount of $^{225}$Ac-lintuzumab may comprise a dose of 0.1 to 10 uCi/kg body weight of the subject, 0.2 to 8 uCi/kg body weight of the subject, 0.5 to 6 uCi/kg body weight of the subject, 0.5 to 4 uCi/kg body weight of the subject, or even 1.5 uCi/kg body weight of the subject.

According to certain aspects of the present invention, the anti-CD33 targeting agent may be administered according to a dosing schedule selected from the group consisting of one every 7, 10, 12, 14, 20, 24, 28, 35, and 42 days throughout a treatment period, wherein the treatment period includes at least two doses.

According to certain aspects of the present invention, the anti-CD33 targeting agent may be administered according to a dose schedule that includes 2 doses, such as on days 1 and 5, 6, 7, 8, 9, or 10 of a treatment period, or days 1 and 8 of a treatment period.

According to certain aspects of the present invention, the anti-CD33 targeting agent may be administered as a single bolus or infusion in a single subject specific dose.

According to certain aspects of the present invention, the methods may further comprise administering to the subject a second therapeutic agent, wherein administration of the second therapeutic agent may be simultaneous or sequential with administration of the anti-CD33 targeting agent. As example, the second therapeutic agent may comprise a second antibody such as an anti-CD45 antibody (e.g., BC8). The second antibody may be at least partially labelled with a radioisotope (e.g., $^{131}$I-BC8 or $^{225}$Ac-BC8).

According to certain aspects of the present invention, the methods may further comprise administration of one or more further therapeutic agents, such as a chemotherapeutic agent, an anti-inflammatory agent, an immunosuppressive, an immunomodulatory agent, antimyeloma agent, a cytokine, or a combination thereof.

According to certain aspects, the further therapeutic agent may be a chemotherapeutic agent administered after the anti-CD33 targeting agent but before transplantation with allogeneic stem cells.

According to certain aspects of the present invention, the anti-CD33 targeting agent may be a portion of a multi-specific antibody. Thus, the methods may include administering to the subject an effective amount of a multi-specific antibody, wherein the multi-specific antibody comprises: a first target recognition component which specifically binds to an epitope of CD33, and a second target recognition component which specifically binds to a different epitope of CD33 than the first target recognition component, or an epitope of a different antigen.

The objects of the present invention will be realized and attained by means of the combinations specifically outlined in the appended claims. The foregoing general description and the following detailed description and examples of this invention are provided to illustrate various aspects of the present invention, and by no means are to be viewed as limiting any of the described embodiments.

BRIEF DESCRIPTION OF THE DRAWINGS

FIG. 1 provides the amino acid sequence of human CD33 as shown in GenBank accession number NP 001763.

DETAILED DESCRIPTION OF THE INVENTION

The presently disclosed invention provides methods for treatment of hematological diseases or disorders in patients having a p53 mutation, or in patients who present poor or very poor cytogenetic groups. The methods generally include administering to the patient an effective amount of a targeting agent which specifically binds to an epitope of CD33 (anti-CD33 targeting agent, antibody fragment, peptide, Fab fragment, aptamer, etc). Such treatment may be an effective precursor to transplantation with allogeneic stem cells, and may provide improved treatment outcomes for a category of patients having poor outcomes with standard prior art therapies (i.e., radiation and/or chemotherapy).

Definitions

In this application, certain terms are used which shall have the meanings set forth as follows.

The singular forms "a," "an," "the" and the like include plural referents unless the context clearly dictates otherwise. Thus, for example, reference to "an" antibody includes both a single antibody and a plurality of different antibodies.

The word "comprising" and forms of the word "comprising", as used in this description and in the claims, does not limit the present invention to exclude any variants or additions. Additionally, although the present invention has been described in terms of "comprising", the processes, materials, and compositions detailed herein may also be described as consisting essentially of or consisting of. For example, while certain aspects of the invention have been described in terms of a method comprising administering a monoclonal antibody against CD33, a method "consisting essentially of" or "consisting of" administering the monoclonal antibody against CD33 is also within the present scope. In this context, "consisting essentially of" means that any additional components will not negatively affect the efficacy of the method.

Moreover, other than in the examples, or where otherwise indicated, all numbers expressing, for example, quantities of ingredients used in the specification are to be understood as being modified in all instances by the term "about". Accordingly, unless indicated to the contrary, the numerical parameters set forth in the following specification are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques. Thus, the term "about" when used before a numerical designation, e.g., temperature, time, amount, and concentration, including a range, indicates approximations which may vary by ±10%, ±5%, or ±1%.

As used herein, "administer", with respect to a targeting agent such as an antibody, antibody fragment, Fab fragment, or aptamer, means to deliver the agent to a subject's body via any known method suitable for antibody delivery. Specific modes of administration include, without limitation, intravenous, transdermal, subcutaneous, intraperitoneal, intrathecal and intra-tumoral administration. Exemplary administration methods for antibodies may be as substantially described in International Publication No. WO 2016/187514, incorporated by reference herein.

In addition, in this invention, antibodies can be formulated using one or more routinely used pharmaceutically acceptable carriers. Such carriers are well known to those skilled in the art. For example, injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's).

As used herein, the term "antibody" includes, without limitation, (a) an immunoglobulin molecule comprising two heavy chains and two light chains and which recognizes an antigen; (b) polyclonal and monoclonal immunoglobulin molecules; (c) monovalent and divalent fragments thereof (e.g., di-Fab), and (d) bi-specific forms thereof. Immunoglobulin molecules may derive from any of the commonly known classes, including but not limited to IgA, secretory IgA, IgG and IgM. IgG subclasses are also well known to those in the art and include, but are not limited to, human IgG1, IgG2, IgG3 and IgG4. Antibodies can be both naturally occurring and non-naturally occurring (e.g., IgG-Fc-silent). Furthermore, antibodies include chimeric antibodies, wholly synthetic antibodies, single chain antibodies, and fragments thereof. Antibodies may be human, humanized or nonhuman.

As used herein, "Immunoreactivity" refers to a measure of the ability of an immunoglobulin to recognize and bind to a specific antigen. "Specific binding" or "specifically binds" or "binds" refers to an antibody binding to an antigen or an epitope within the antigen with greater affinity than for other antigens. Typically, the antibody binds to the antigen or the epitope within the antigen with an equilibrium dissociation constant ($K_D$) of about $1 \times 10^{-8}$ M or less, for example about $1 \times 10^{-9}$ M or less, about $1 \times 10^{-10}$ M or less, about $1 \times 10^{-11}$ M or less, or about $1 \times 10^{-12}$ M or less, typically with the $K_D$ that is at least one hundred fold less than its $K_D$ for binding to a nonspecific antigen (e.g., BSA, casein). The dissociation constant may be measured using standard procedures. Antibodies that specifically bind to the antigen or the epitope within the antigen may, however, have cross-reactivity to other related antigens, for example to the same antigen from other species (homologs), such as human or monkey, for example *Macaca fascicularis* (cynomolgus, cyno), Pan troglodytes (chimpanzee, chimp) or *Callithrix jacchus* (common marmoset, marmoset).

As used herein, an "anti-CD33 targeting agent" is an antibody, antibody fragment, peptide, Fab fragment, or aptamer that binds to any available epitope of CD33. According to certain aspects, the anti-CD33 targeting agent is a humanized antibody against CD33, such as lintuzumab (HuM195), gemtuzumab, or vadastuximab. According to certain aspects, the anti-CD33 targeting agent binds to the epitope recognized by the monoclonal antibody "lintuzumab" or "HuM195." HuM195 is known, as are methods of making it.

An "epitope" refers to the target molecule site (e.g., at least a portion of an antigen) that is capable of being recognized by, and bound by, a targeting agent such as an antibody, antibody fragment, Fab fragment, or aptamer. For a protein antigen, for example, this may refer to the region of the protein (i.e., amino acids, and particularly their side chains) that is bound by the antibody. Overlapping epitopes include at least one to five common amino acid residues. Methods of identifying epitopes of antibodies are known to those skilled in the art and include, for example, those described in Antibodies, A Laboratory Manual, Cold Spring Harbor Laboratory, Ed Harlow and David Lane (1988).

As used herein, "cancer" includes, without limitation, a solid cancer (e.g., a tumor) and a hematologic malignancy.

A "hematologic disease" or "hematological disorder" may be taken to refer to at least a blood cancer. Such cancers originate in blood-forming tissue, such as the bone marrow or other cells of the immune system. A hematologic disease or disorder includes, without limitation, leukemias (such as acute myeloid leukemia (AML), acute promyelocytic leukemia, acute lymphoblastic leukemia (ALL), acute mixed lineage leukemia, chronic myeloid leukemia, chronic lymphocytic leukemia (CLL), hairy cell leukemia and large granular lymphocytic leukemia), myelodysplastic syndrome (MDS), myeloproliferative disorders (polycythemia vera, essential thrombocytosis, primary myelofibrosis and chronic myeloid leukemia), lymphomas, multiple myeloma, MGUS and similar disorders, Hodgkin's lymphoma, non-Hodgkin lymphoma (NHL), primary mediastinal large B-cell lymphoma, diffuse large B-cell lymphoma, follicular lymphoma, transformed follicular lymphoma, splenic marginal zone lymphoma, lymphocytic lymphoma, T-cell lymphoma, and other B-cell malignancies.

"Solid cancers" include, without limitation, bone cancer, pancreatic cancer, skin cancer, cancer of the head or neck, cutaneous or intraocular malignant melanoma, uterine cancer, ovarian cancer, prostate cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, pediatric tumors, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally-induced cancers including those induced by asbestos.

As used herein, the term "complex karyotype" may be taken to indicate the presence of more than or equal to 3 chromosomal aberrations, or more than or equal to 5 chromosomal aberrations.

According to certain aspects, the anti-CD33 targeting agent may be labelled with a radioisotope. Methods of labeling these proteins such as antibodies with radioisotopes, such as the radioisotopes $^{131}$I or $^{225}$Ac, are known. These methods are described, for example, in International Publication No. WO 2017/155937.

As used herein, a "radioisotope" can be an alpha-emitting isotope, a beta-emitting isotope, and/or a gamma-emitting isotope. Examples of radioisotopes include the following: $^{131}$I, $^{125}$I, $^{123}$I, $^{90}$Y, $^{177}$Lu, $^{186}$Re, $^{188}$Re, $^{89}$Sr, $^{153}$Sm, $^{32}$P, $^{225}$Ac, $^{213}$Bi, $^{213}$Po, $^{211}$At, $^{212}$Bi, $^{213}$Bi, $^{223}$Ra, $^{227}$Th, $^{149}$Tb, $^{137}$Cs, $^{212}$Pb and $^{103}$Pd. Methods for affixing a radioisotope to an antibody or antibody fragment (i.e., "labeling" an antibody with a radioisotope) are well known.

According to certain aspects, the anti-CD33 targeting agent may be an antibody radiolabeled with $^{131}$I ("$^{131}$I-labeled"), and the effective amount may be below, for example, 1200 mCi (i.e., where the amount of $^{131}$I administered to the subject delivers a total body radiation dose of below 1200 mCi). According to certain aspects, when the antibody is $^{131}$I-labeled, the effective amount may be below 1000 mCi, below 750 mCi, below 500 mCi, below 250 mCi, below 200 mCi, below 150 mCi, below 100 mCi, below 50 mCi, below 40 mCi, below 30 mCi, below 20 mCi or below 10 mCi. According to certain aspects of this method, the effective amount of $^{131}$I-labeled antibody is from 10 mCi to 200 mCi. Examples of effective amounts include, without limitation, from 50 mCi to 100 mCi, from 50 mCi to 150 mCi, from 50 mCi to 200 mCi, from 60 mCi to 140 mCi, from 70 mCi to 130 mCi, from 80 mCi to 120 mCi, from 90 mCi to 110 mCi, from 100 mCi to 150 mCi, 50 mCi, 60 mCi, 70 mCi, 80 mCi, 90 mCi, 100 mCi, 110 mCi, 120 mCi, 130 mCi, 140 mCi, 150 mCi, or 200 mCi. According to certain aspects of this method, the effective amount of $^{131}$I-labeled antibody is from 200 mCi to 1200 mCi. Examples of effective amounts include, without limitation, from 200 mCi to 300 mCi, from 200 mCi to 400 mCi, from 200 mCi to 500 mCi, from 200 mCi to 600 mCi, from 200 mCi to 700 mCi, from 200 mCi to 800 mCi, from 200 mCi to 900 mCi, from 200 mCi to 1000 mCi, from 200 mCi to 1100 mCi, from 300 mCi to 1200 mCi, from 400 mCi to 1200 mCi, from 500 mCi to 1200 mCi, from 600 mCi to 1200 mCi, from 700 mCi to 1200 mCi, from 800 mCi to 1200 mCi, from 900 mCi to 1200 mCi, from 1000 mCi to 1200 mCi, 50 mCi, 100 mCi, 150 mCi, 200 mCi, 300 mCi, 400 mCi, 500 mCi, 600 mCi, 700 mCi, 800 mCi, 900 mCi, 1000 mCi, or 1100 mCi.

According to certain aspects, anti-CD33 targeting agent may be an antibody radiolabeled with $^{225}$Ac ("$^{225}$Ac-labeled"), and the effective amount may be below, for example, 5.0 µCi/kg (i.e., where the amount of $^{225}$Ac administered to the subject delivers a radiation dose of below 5.0 µCi per kilogram of subject's body weight). According to certain aspects, when the antibody is $^{225}$Ac-labeled, the effective amount is below 4.5 µCi/kg, 4.0 µCi/kg, 3.5 µCi/kg, 3.0 µCi/kg, 2.5 µCi/kg, 2.0 µCi/kg, 1.5 µCi/kg, 1.0 µCi/kg, 0.9 µCi/kg, 0.8 µCi/kg, 0.7 µCi/kg, 0.6 µCi/kg, 0.5 µCi/kg, 0.4 µCi/kg, 0.3 µCi/kg, 0.2 µCi/kg, 0.1 µCi/kg or 0.05 µCi/kg. According to certain aspects, when the antibody is $^{225}$Ac-labeled, the effective amount is from 0.05 µCi/kg to 0.1 µCi/kg, from 0.1 µCi/kg to 0.2 µCi/kg, from 0.2 µCi/kg to 0.3 µCi/kg, from 0.3 µCi/kg to 0.4 µCi/kg, from 0.4 µCi/kg to 0.5 µCi/kg, from 0.5 µCi/kg to 0.6 µCi/kg, from 0.6 µCi/kg to 0.7 µCi/kg, from 0.7 µCi/kg to 0.8 µCi/kg, from 0.8 µCi/kg to 0.9 µCi/kg, from 0.9 µCi/kg to 1.0 µCi/kg, from 1.0 µCi/kg to 1.5 µCi/kg, from 1.5 µCi/kg to 2.0 µCi/kg, from 2.0 µCi/kg to 2.5 µCi/kg, from 2.5 µCi/kg to 3.0 µCi/kg, from 3.0 µCi/kg to 3.5 µCi/kg, from 3.5 µCi/kg to 4.0 µCi/kg, from 4.0 µCi/kg to 4.5 µCi/kg, or from 4.5 µCi/kg to 5.0 µCi/kg. According to certain aspects, when the antibody is $^{225}$Ac-labeled, the effective amount is 0.05 µCi/kg, 0.1 µCi/kg, 0.2 µCi/kg, 0.3 µCi/kg, 0.4 µCi/kg, 0.5 µCi/kg, 0.6 µCi/kg, 0.7 µCi/kg, 0.8 µCi/kg, 0.9 µCi/kg, 1.0 µCi/kg, 1.5 µCi/kg, 2.0 µCi/kg, 2.5 µCi/kg, 3.0 µCi/kg, 3.5 µCi/kg, 4.0 µCi/kg or 4.5 µCi/kg.

According to certain aspects of the present invention, when the anti-CD33 targeting agent is labeled with a radioisotope, the majority of the targeting agent (antibody, antibody fragment, etc.) administered to a subject typically consists of non-labeled targeting agent, with the minority being the labeled targeting agent. The ratio of labeled to non-labeled targeting agent can be adjusted using known methods. Thus, accordingly to certain aspects of the present invention, the anti-CD33 targeting agent may be provided in a total protein amount of up to 100 mg, such as up to 60 mg, such as 5 mg to 45 mg, or a total protein amount of between 0.01 mg/kg patient weight to 15.0 mg/kg patient weight, such as between 0.01 mg/kg patient weight to 1.0 mg/kg, or between 0.2 mg/kg patient weight to 0.6 mg/kg patient weight, or 0.3 mg/kg patient weight, or 0.4 mg/kg patient weight, or 0.5 mg/kg patient weight.

According to certain aspects of the present invention, when the anti-CD33 targeting agent is radiolabeled, the radiolabeled anti-CD33 targeting agent may comprise a labeled fraction and an unlabeled fraction, wherein the ratio of labeled:unlabeled may be from about 0.01:10 to 1:1, such as 0.1:10 to 1:1 labeled:unlabeled. Moreover, the radiolabeled anti-CD33 targeting agent may be provided as a single dose composition tailored to a specific patient, wherein the amount of labeled and unlabeled anti-CD33 targeting agent in the composition may depend on at least a patient weight, age, and/or disease state or health status, such as detailed in International Publication No. WO 2016/187514.

As used herein, the term "subject" includes, without limitation, a mammal such as a human, a non-human primate, a dog, a cat, a horse, a sheep, a goat, a cow, a rabbit, a pig, a rat and a mouse. Where the subject is human, the subject can be of any age. For example, the subject can be 60 years or older, 65 or older, 70 or older, 75 or older, 80 or older, 85 or older, or 90 or older. Alternatively, the subject can be 50 years or younger, 45 or younger, 40 or younger, 35 or younger, 30 or younger, 25 or younger, or 20 or younger. For a human subject afflicted with cancer, the subject can be newly diagnosed, or relapsed and/or refractory, or in remission.

As used herein, "treating" a subject afflicted with a cancer shall include, without limitation, (i) slowing, stopping or reversing the cancer's progression, (ii) slowing, stopping or reversing the progression of the cancer's symptoms, (iii) reducing the likelihood of the cancer's recurrence, and/or (iv) reducing the likelihood that the cancer's symptoms will recur. According to certain preferred aspects, treating a subject afflicted with a cancer means (i) reversing the cancer's progression, ideally to the point of eliminating the cancer, and/or (ii) reversing the progression of the cancer's symptoms, ideally to the point of eliminating the symptoms, and/or (iii) reducing or eliminating the likelihood of relapse (i.e., consolidation, which ideally results in the destruction of any remaining cancer cells).

"Chemotherapeutic", in the context of this invention, shall mean a chemical compound which inhibits or kills growing cells and which can be used or is approved for use in the treatment of cancer. Exemplary chemotherapeutic agents include cytostatic agents which prevent, disturb, disrupt or delay cell division at the level of nuclear division or cell plasma division. Such agents may stabilize microtubules, such as taxanes, in particular docetaxel or paclitaxel, and epothilones, in particular epothilone A, B, C, D, E, and F, or may destabilize microtubules such as vinca alcaloids, in particular vinblastine, vincristine, vindesine, vinflunine, and vinorelbine.

"Therapeutically effective amount" or "effective amount" refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Exemplary indicators of an effective therapeutic or combination of therapeutics include, for example, improved well-being of the patient, reduction in a tumor burden, arrested or slowed growth of a tumor, and/or absence of metastasis of cancer cells to other locations in the body. According to certain aspects, "therapeutically effective amount" or "effective amount" refers to an amount of the anti-CD33 targeting agent that may deplete or cause a reduction in the overall number of cells expressing CD33, or may inhibit growth of cells expressing CD33.

As used herein, "depleting", with respect to cells expressing CD33, shall mean to lower the population of at least one type of cells that express of overexpress CD33 (e.g., at least one type of the subject's peripheral blood lymphocytes or at least one type of the subject's bone marrow lymphocytes). According to certain aspects of this invention, a subject's lymphocyte decrease is determined by measuring the subject's peripheral blood lymphocyte level. As such, and by way of example, a subject's lymphocyte population is depleted if the population of at least one type of the subject's peripheral blood lymphocytes is lowered, such as by at least 10%, 20%, 30%, 40%, 50%, 60%, 70%, 80%, 90% or 99%.

"Inhibits growth" refers to a measurable decrease or delay in the growth of a malignant cell or tissue (e.g., tumor) in vitro or in vivo when contacted with a therapeutic or a combination of therapeutics or drugs, when compared to the decrease or delay in the growth of the same cells or tissue in the absence of the therapeutic or the combination of therapeutic drugs. Inhibition of growth of a malignant cell or tissue in vitro or in vivo may be at least about 10%, 20%, 30%, 40%, 50%, 60%, 70%, 80%, 90%, 95%, 96%, 97%, 98%, 99%, or 100%.

The term "p53 protein" as used herein refers to both the p53 protein and the TP53 gene, and "p53 mutations" refers to mutations in either or both of the p53 protein and the TP53 gene. P53 is the tumor suppressor protein encoded by the TP53 gene in humans.

Mutant TP53 genes or gene products (i.e., p53 protein) can be detected in tumor samples or, in some types of cancer, in biological samples such as urine, stool, sputum or serum. Cancer cells are found in blood and serum for cancers such as lymphoma or leukemia. A TP53 gene mutation in a sample can be identified using any method known in the art. One of the most commonly used methods to "identify" p53 mutants is by utilizing immunohistochemistry on tumor sections stained with a p53 antibody. In another assay, nucleic acid from the sample is contacted with a nucleic acid probe that is capable of specifically hybridizing to nucleic acid encoding a mutated p53 protein, or fragment thereof incorporating a mutation, and detecting the hybridization.

According to certain aspects, the probe is detectably labeled such as with a fluorescent agent (rhodamine, fluorescene) or a chromogenic agent. In a particular embodiment the probe is an antisense oligomer. The probe may be from about 8 nucleotides to about 100 nucleotides, or about 10 to about 75, or about 15 to about 50, or about 20 to about 30. Kits for identifying p53 mutations in a sample are available that include an oligonucleotide that specifically hybridizes to or adjacent to a site of mutation in the p53 gene. The p53 Amplichip™ developed by Roche is a good example of such technology.

A mutation in the TP53 gene can also be detected by amplifying nucleic acid corresponding to the TP53 gene obtained from the sample, or a biologically active fragment, and comparing the electrophoretic mobility of the amplified nucleic acid to the electrophoretic mobility of corresponding wild-type TP53 gene or fragment thereof. A difference in the mobility indicates the presence of a mutation in the amplified nucleic acid sequence. Electrophoretic mobility may be determined on polyacrylamide gel.

Alternatively, an amplified TP53 gene or fragment nucleic acid may be analyzed for detection of mutations using enzymatic mutation detection, which uses the bacteriophage resolvase T4 endonuclease VII, which scans along double-stranded DNA until it detects and cleaves structural distortions caused by base pair mismatches resulting from point mutations, insertions and deletions. Detection of two short fragments formed by resolvase cleavage, for example by gel electrophoresis, indicates the presence of a mutation. Benefits of the enzymatic mutation detection method are a single protocol to identify point mutations, deletions, and insertions assayed directly from PCR reactions eliminating the need for sample purification, shortening the hybridization time, and increasing the signal-to-noise ratio. Mixed samples containing up to a 20-fold excess of normal DNA and fragments up to 4 kb in size can been assayed.

In order to detect such mutations, a sample or biopsy of the tumor or a sample comprising cancer cells or precancerous cells (such as blood, serum, CSF, stool, urine or sputum) is obtained by methods well known in the art and appropriate for the particular type and location of the tumor, Means for enriching a tissue preparation for tumor cells are known in the art. For example, the tissue may be isolated from paraffin or cryostat sections. Cancer cells may also be separated from normal cells by flow cytometry or laser capture microdissection. These as well as other techniques for separating tumor from normal cells are well known in the art. If the tumor tissue is highly contaminated with normal cells, detection of mutations is more difficult.

Detection of point mutations may be accomplished by molecular cloning of the p53 allele (or alleles) and sequencing that allele(s) using techniques well known in the art. Alternatively, the polymerase chain reaction can be used to amplify gene sequences directly from a genomic DNA preparation from the tumor tissue. The DNA sequence of the amplified sequences can then be determined and mutations identified. The polymerase chain reaction is well known in the art.

Alteration of wild-type p53 genes can also be detected by screening for alteration of wild-type p53 protein. For example, monoclonal antibodies immunoreactive with p53 can be used to screen a tissue. Antibodies specific for products of mutant alleles could also be used to detect mutant p53 gene product(s). Such immunological assays can be done in any convenient format known in the art. These include Western blots, immunohistochemical assays and ELISA assays. Any means for detecting an altered p53 protein or p53 mRNA can be used to detect alteration of wild-type p53 genes or the expression product of the gene.

As used herein, the term "determining", when used with reference to the presence of a p53 mutation may be taken to include detecting the presence of a p53 mutation using any of the methods disclosed herein or known in the art, and/or noting the presence of a p53 mutation based on prior detection by another (e.g., prior detection by a subject's doctor, or as part of another study or treatment protocol, etc.).

The term "sample" as used herein includes any biological specimen obtained from a subject. Samples include, without limitation, whole blood, plasma, serum, red blood cells, white blood cells (e.g., peripheral blood mononuclear cells), saliva, urine, stool (i.e., feces), tears, nipple aspirate, lymph, fine needle aspirate, any other bodily fluid, a tissue sample (e.g., tumor tissue) such as a biopsy of a tumor, and cellular extracts thereof in some embodiments, the sample is whole blood or a fractional component thereof such as plasma, serum, or a cell pellet in certain embodiments, the sample is obtained by isolating circulating cells of a solid tumor from a whole blood cell pellet using any technique known in the art. As used herein, the term "circulating cancer cells" comprises cells that have either metastasized or micro metastasized from a solid tumor and includes circulating tumor cells, and cancer stem cells. In other embodiments, the sample is a formalin fixed paraffin embedded tumor tissue sample, e.g., from a solid tumor.

Throughout this application, various publications are cited. The disclosure of these publications is hereby incorporated by reference into this application to describe more fully the state of the art to which this invention pertains.

Unless otherwise defined, all technical and scientific terms used herein have the same meaning as commonly understood by one of ordinary skill in the art to which the present invention belongs. Although methods and materials similar or equivalent to those described herein can be used in the practice or testing described herein, suitable methods and materials are described below.

ASPECTS OF THE INVENTION

The present inventors have found that targeted myeloconditioning or myeloablation with anti-CD33 targeting agents may offer successful disease eradication prior to transplantation in a more tolerable manner than more intensive prior art chemotherapy or total body irradiation conditioning regimens. This particularly applies to the patient group with higher risk MDS based on cytogenetic prognostic grouping, and those with genetic mutations of TP53, which have poorer outcomes despite undergoing HSCT and standard myeloablative conditioning and reduced intensity conditioning. Accordingly, the present invention relates to methods of treating a subject having a proliferative disorder by administration of an immunotherapeutic agent against an epitope of CD33, and more specifically, to administration of an anti-CD33 targeting agent, such as an antibody, antibody fragment, Fab fragment, and/or aptamer, for the treatment of certain hematological diseases, such as myelodysplastic syndromes (MDS), in patients exhibiting poor or very poor cytogenetic profiling, and/or those with genetic mutations of TP53.

Patients with myelodysplastic syndromes (MDS) in the poor and very poor cytogenetic prognostic groups constitute approximately 45% of patients with MDS who receive allogeneic HSCT. MDS patients in the cytogenic prognostic group of "very poor" have a median survival of 4.6 months and patients in the "poor" group have a median survival 16.7 months.

Anti-CD33 antibodies such as lintuzumab, when radiolabeled, target and irradiate certain hematological cells using alpha particles, which have very high energy released over a very short path length. For example, the present inventors have found that Lintuzumab-$^{225}$Ac represents an effective therapeutic for destroying CD33 positive MDS cells prior to HSCT, leading to reduced relapse rates after allogeneic HSCT. MDS patients undergoing allogeneic HSCT have often received prior treatment with hypomethylating agents or cytotoxic chemotherapy, but virtually never receive radiation as part of their MDS therapy. Studies using radioactive iodine linked to a CD45 antibody used as conditioning prior to allogeneic HSCT have been performed in patients with MDS with successful engraftment of allogeneic hematopoietic stem cells. Since approximately 96% of patients with MDS express CD33 on the MDS cells, a conditioning agent targeting radiation to CD33 positive cells represents a new approach to eradicating MDS cells prior to allogeneic HSCT, either alone or in combination with additional agents.

Overexpression of CD33 is commonly found in many hematological malignancies, including AML and MDS. In AML, the majority of patients strongly express CD33, which has led to the development of targeted therapies, such as gemtuzumab-ozogamicin (Mylotarg). Moreover, approximately 96% of MDS patients express CD33 on their myeloblasts (Sanford et al., "CD33 is frequently expressed in cases of myelodysplastic syndrome and chronic myelomonocytic leukemia with elevated blast count," 2016, Leukemia & Lymphoma, vol. 57(8):1965-1968). In another study of CD33 molecules in bone marrow, MDS patients demonstrated approximately twice as many CD33 molecules per bone marrow cell as the control samples (Jilani, et al., "Differences in CD33 intensity between various myeloid neoplasms," 2002, Am J Clin Pathol 2002, vol. 118:560-566).

Accordingly, the present invention is related to methods for treating myelodysplastic syndrome in a subject by administering an effective amount of an anti-CD33 targeting agent to the subject.

The present invention is also related to methods for treating high-risk or advanced myelodysplastic syndrome according to the international prognostic scoring system (IPSS-R), wherein the method comprises administering to a subject having high-risk or advanced myelodysplastic syndrome a therapeutically effective amount of an anti-CD33 targeting agent; or administering to a subject having myelodysplastic syndrome a therapeutically effective amount of an anti-CD33 targeting agent, wherein the subject is in the poor or very poor cytogenetic prognostic groups, as defined by the IPSS-R.

The p53 tumor suppressor is a 393-amino acid transcription factor. In response to various types of genotoxic stresses, p53 transactivates a number of genes by binding to specific DNA sequences, thereby arresting cell cycle, repairing damaged DNA, or inducing apoptosis. The activity of the p53 protein is regulated by posttranslational mechanisms such as phosphorylation, methylation, acetylation, and prolyl-isomerisation, or by protein-protein interaction.

The p53 protein is composed of 6 functional domains. The amino-terminal residues one (1) to 42 and 43 to 63 contain two transactivation domains. The first can be bound by MDM2, a negative regulator of p53, and the second can bind to p53-responsive elements in promoters of different p53-regulated genes to activate their transcription. The proline-rich domain spanning residues 61-94 is involved in apoptosis and protein-protein interactions. The largest domain includes residues 102-292 and functions in binding p53-responsive sequences associated with genes regulated by p53. The p53 protein functions as a tetramer, and tetramerization is accomplished by residues 324-355. The carboxy-terminal domain from residue 363 to 393 regulates the stability and DNA binding activity of the p53 protein.

Somatic p53 mutations are the most common (about 50%) genetic alteration in human cancer, and a large number of p53 mutations have been assembled in p53 mutation databases. A p53 mutation according to the present invention may be defined as any mutation in the genetic set-up of the tumor cell which affects the primary amino acid sequence of the p53 protein and decreases apoptosis induction activity of the p53 protein (point, insertion, deletion, and/or inversion). It follows that the p53 mutations according to the present invention include all mutations resulting in frameshifts and all deletions and insertions in the coding region. Moreover, all single base substitutions in the coding area which result in a change in primary amino acid sequence are p53 mutations according to the present invention as well as mutations in the regulating regions which cause loss or decreased expression of the p53 protein in comparison to healthy tissue. Finally, all mutations affecting splice sites, thereby resulting in p53 proteins with different amino acid sequence, are also included. A p53 mutation according to the present invention may also be defined as any mutation in the genetic set-up of the tumor cell which affects overall expression of the p53 protein and thus decreases apoptosis induction activity of the p53 protein Accordingly, the methods of the present invention may also be used to improve the treatment outcomes for patients with a proliferative disease or disorder who also have a mutated p53 gene, a mutant form of the p53 protein, or a mutation that may lead to reduced expression of the p53 protein, and thus reduced apoptosis induction.

As such, the present invention is further related to methods for treating a proliferative disease in a subject having a have a mutation in the p53 tumor suppressor ("mutant p53"), wherein the method comprises administering an effective amount of an anti-CD33 targeting agent to the subject.

The methods of the present invention may include screening for the presence of a mutated p53 gene or mutant form of the p53 protein prior to proceeding with administration of the anti-CD33 targeting agent.

According to certain aspects of the present invention, the methods may include obtaining a sample of cells from the subject, such as cancer cells, precancerous cells, or cells from a tumor. These cells may be screened or assayed for the presence of a mutated p53 gene or a mutant form of p53 protein. If it is determined that the cells have a mutated p53 gene or mutant form of the p53 protein, the method may include proceeding with administration of the effective amount of the anti-CD33 targeting agent.

According to the methods of the present invention, the proliferative disease or disorder may be a hematological disease or disorder. The hematological disease or disorder may comprise myelodysplastic syndrome (MDS), multiple myeloma (MM), acute myeloid leukemia (AML), chronic myeloid leukemia (CML), chronic lymphocytic leukemia (CLL), acute lymphoblastic leukemia (ALL), non-Hodgkin lymphoma (NHL), and Hodgkin lymphoma (HL). According to certain aspects of the present invention, the hematological disease or disorder may comprise myelodysplastic syndrome, relapsed and/or refractory multiple myeloma, or acute myeloid leukemia.

The methods disclosed herein may be used to treat a patient having myelodysplastic syndrome. The methods disclosed herein may be used to inhibit growth and/or proliferation of a cell expressing CD33. The methods disclosed herein may also be used to treat a disease or disorder involving cells expressing or overexpressing CD33.

Human CD33 has an amino acid sequence shown in GenBank accession number NP_001763 and in SEQ ID NO: 1 (FIG. 1). CD33 is a 67 Kd type I transmembrane receptor glycoprotein that may function as a sialic acid-dependent cell adhesion molecule. CD33 has a long N-terminal extracellular domain, a helical transmembrane domain, and a short C-terminal cytoplasmic domain. Expressed on early myeloid progenitor and myeloid leukemic (e.g., acute myelogenous leukemia, AML) cells, CD33 is not expressed on stem cells.

With reference to FIG. 1, amino acid residues 1-259 represent the extracellular domain, amino acids 260-282 represent the helical transmembrane domain, and amino acids 283-364 represent the cytosolic domain (intracellular). There are at least three known single nucleotide polymorphisms ("SNPs") in the extracellular domain of CD33 (i.e., W22R, R69G, S128N). Therefore, the extracellular domain of *Homo sapiens* CD33 can have the amino acid sequence of SEQ ID NO: 1 with any one or more of these SNPs.

The CD33 protein has structural similarity to immunoreceptors, and its normal function is thought to serve as a negative regulator of immunoreceptor (ITAM) signal transduction. Recent studies suggest a role for CD33 in the modulation of inflammatory and immune responses through a dampening effect on tyrosine kinase-driven signaling pathways. For example, in vitro studies have demonstrated that CD33 constitutively suppresses the production of pro-inflammatory cytokines such as IL-113, TNF-α, and IL-8 by human monocytes in a sialic acid ligand-dependent and SOCS3-dependent manner. Conversely, reduction of cell surface CD33 or interruption of sialic acid binding can increase p38 mitogen-activated protein kinase (MAPK) activity and enhance cytokine secretion as well as cytokine-induced cellular proliferation.

Antibodies against CD33, such as lintuzumab (HuM195), gemtuzumab, and vadastuximab have been, and are currently being evaluated in the clinic for their efficacy to treat hematological malignancies and plasma cell disorders, including acute myeloid leukemia (AML). Each antibody has been found to bind to a different portion of the extracellular region of CD33, and each demonstrates different clinical responses (e.g., anti-tumor effects). Gemtuzumab is available from Pfizer as Mylotarg™, and vadastuximab is available from Seattle Genetics as Vadastuximab talirine.

For example, the antibody lintuzumab (HuM195) has demonstrated anti-leukemic effects in treatment of AML. HuM195 is a recombinant humanized anti-CD33 monoclonal antibody originally produced by Protein Design Labs, Inc. (Fremont, Calif.). M195 is a monoclonal IgG2a antibody that binds CD33. M195 is derived from a mouse immunized with live human leukemic myeloblasts. HuM195 was constructed by grafting complementarity-determining regions of M195 into a human IgG1 framework and backbone. HuM195 induced antibody-dependent cell-mediated cytotoxicity using human peripheral blood mononuclear cells as effectors. Four clinical trials have investigated native (i.e., unconjugated) HuM195 alone in patients with relapsed or refractory AML and CML. Fever, chills, and nausea were the most common toxicities. Human anti-human antibody responses were not seen. Beneficial biologic activity in terms of reduction in marrow blast cells was seen in some patients. Those who benefited the most had fewer blasts at the beginning of therapy, suggesting that HuM195 may be more effective in the treatment of minimal residual or cytoreduced disease.

Proposed methods by which antibodies eliminate CD33-positive cells include antibody-dependent cellular cytotoxicity (ADCC), complement-dependent cytotoxicity (CDC), and apoptosis.

"Antibody-dependent cellular cytotoxicity", "antibody-dependent cell-mediated cytotoxicity" or "ADCC" is a mechanism for inducing cell death that depends upon the interaction of antibody-coated target cells with effector cells possessing lytic activity, such as natural killer (NK) cells, monocytes, macrophages and neutrophils via Fc gamma receptors (FcγR) expressed on effector cells. For example, NK cells express FcγRIIIa, whereas monocytes express FcγRI, FcγRII and FcvRIIIa. Death of the antibody-coated target cell, such as CD33-expressing cells, occurs as a result of effector cell activity through the secretion of membrane pore-forming proteins and proteases.

"Complement-dependent cytotoxicity", or "CDC", refers to a mechanism for inducing cell death in which an Fc effector domain of a target-bound antibody binds and activates complement component C1q, which in turn activates the complement cascade leading to target cell death. Activation of complement may also result in deposition of complement components on the target cell surface that facilitate ADCC by binding complement receptors (e.g., CR3) on leukocytes.

"Apoptosis" refers to a mechanism of programmed cell death wherein antibody binding to the target cell disrupts integral cell signaling pathways and results in cell self-destruction.

To assess ADCC activity of an antibody that binds to a specific antigen, such as an antibody against CD33, the antibody may be added to antigen-expressing cells in combination with immune effector cells, which may be activated by the antigen-antibody complexes resulting in cytolysis of the antigen-expressing cells, respectively. Cytolysis is generally detected by the release of a label (e.g. radioactive substrates, fluorescent dyes or natural intracellular proteins) from the lysed cells. Exemplary effector cells for such assays include peripheral blood mononuclear cells (PBMC) and NK cells.

As example, in an exemplary assay for ADCC activity of an anti-CD33 targeting agent, CD33-expressing cells may be labeled with $^{51}$Cr and washed extensively. The anti-CD33 antibodies may be added to the CD33-expressing cells at various concentrations, and the assay started by adding effector cells (NK cells from peripheral blood mononuclear cells, for example). After incubation for various time intervals at 37° C., assays are stopped by centrifugation and $^{51}$Cr release from lysed cells is measured in a scintillation counter. The percentage of cellular cytotoxicity may be calculated as the percent maximal lysis which may be induced by adding 3% perchloric acid to the CD33-expressing cells.

In an exemplary assay for cytotoxicity, tetrazolium salt may be added to the CD33-expressing cells treated with various amounts of the anti-CD33 targeting agent. In living mitochondria, the XTT is reduced to an orange product by mitochondrial dehydrogenase and transferred to the cell surface. The orange product can be optically quantified and reflects the number of living cells. Alternatively, esterases from living cells are known to hydrolyze the colorless calcenin into as fluorescent molecule. The fluorescence can be measured and quantified, and reflects the number of living cells in the sample. The total amount of dead cells may be measured using propidium iodide, which is excluded from live cells by intact membranes. The fluorescence due to the propidium iodide in dead cells may be quantified by flow-cytometry.

In order to assess CDC, complement protein may need to be included in an assay for cytotoxicity. Measurement of apoptosis induction does not require addition of NK cells or complement protein in an assay for cytotoxicity.

Thus, the present invention contemplates the treatment of proliferative diseases or disorders, such as hematological diseases or disorders, with monoclonal antibodies against an epitope of CD33 which may function to reduce the number of or kill cells expressing CD33. Methods of the present invention comprise administration of an effective amount of the anti-CD33 targeting agent.

The present invention further contemplates methods of treating a proliferative disease or disorder which includes administration of a multi-specific antibody against two or more epitopes of CD33, or against an epitope of CD33 and epitopes of one or more additional different antigens.

The additional different antigens may be antigens differentially expressed on cells involved in hematological diseases or disorders, and/or cells involved in solid tumors. For example, the additional different antigens may be selected from the group comprising mesothelin, TSHR, CD19, CD123, CD22, CD30, CD45, CD171, CD138, CS-1, CLL-1, GD2, GD3, B-cell maturation antigen (BCMA), Tn Ag, prostate specific membrane antigen (PSMA), ROR1, FLT3, FAP, TAG72, CD38, CD44v6, CEA, EPCAM, B7H3, KIT, IL-13Ra2, interleukin-11 receptor a (IL-1 1Ra), PSCA, PRSS21, VEGFR2, LewisY, CD24, platelet-derived growth factor receptor-beta (PDGFR-beta), SSEA-4, CD20, Folate receptor alpha (FRa), ERBB2 (Her2/neu), MUC1, epidermal growth factor receptor (EGFR), EGFRvIII, NCAM, Prostase, PAP, ELF2M, Ephrin B2, IGF-I receptor, CAIX, LMP2, gplOO, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD 179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, MAGEA3, MAGEA3/A6, ETV6-AML, sperm protein 17, XAGE1, Tie 2, MAD-CT-1, MAD-CT-2, Fos-related antigen 1, prostein, survivin and telomerase, PCTA-1/Galectin 8, KRAS, MelanA/MART1, Ras mutant, hTERT, sarcoma translocation breakpoints, ML-IAP, ERG (TMPRSS2 ETS fusion gene), NA17, PAX3, Androgen receptor, Cyclin B 1, MYCN, RhoC, TRP-2, CYP1B 1, BORIS, SART3, PAX5, OY-TES 1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, GPA7, and IGLL1.

The additional different antigens may be antigens that may induce myeloconditioning such as, for example, CD45. As such, the present invention contemplates methods of treating a proliferative disease or disorder which includes administration of a multi-specific antibody against at least one epitope of CD33, and against at least one epitope of CD45. An exemplary anti-CD45 antibody includes BC8.

Alternatively, the present invention contemplates methods of treating a proliferative disease or disorder which includes administration of a first antibody against at least one antigen of CD33, and administration of a second antibody, wherein the second antibody is against a different epitope of CD33 than the first antibody, or is against an epitope of a different antigen, such as an antigen selected from the list presented above. In an exemplary embodiment, the second antigen may be CD45.

Such combinations, presented as a multi-specific antibody or more than one monoclonal antibody as indicated above, may deliver a synergistic combination that provides a therapeutic effect which is comparable to the effectiveness of a monotherapy with only an antibody against CD33, while reducing adverse side effects of the monotherapy. Moreover, the combination may deliver an improved effectiveness over the monotherapy, which may be measured by reduction in the total tumor cell number, increase in the length of time to relapse, and other indicia of patient health.

When the methods include administration of a multi-specific antibody, the first target recognition component may comprise one of: a first full length heavy chain and a first full length light chain, a first Fab fragment, or a first single-chain variable fragment (scFvs). Moreover, the first target recognition component may be derived from lintuzumab (HuM195), gemtuzumab, or vadastuximab. The second target recognition component may comprise one of: a second full length heavy chain and a second full length light chain, a second Fab fragment, or a second single-chain variable fragment (scFvs). Moreover, the second target recognition component may be derived from a different epitope of the CD33 antigen, or may be derived from any of the antigens listed above.

According to certain aspects of the present invention, the anti-CD33 targeting agent and/or additional antibodies against other antigens, may comprise a radioisotope.

According to certain aspects of the present invention, when the immunotherapy includes a bispecific antibody, either one or both of the first target recognition component and the second target recognition component may comprise a radioisotope.

The targeting agents of the present invention may be labelled with the radioisotope by any means known in the art. According to one aspect of the invention, the radioisotope may be attached or chelated by a chelating agent which is conjugated to the targeting agent (antibody, antibody fragment, etc.) such as substantially described in co-pending provisional Patent Application 62/539,114. That is, the radiolabeled targeting agent may be prepared by first forming a chelator conjugated antibody (or antibody fragment, etc.; "conjugated antibody"), and then chelating a radioisotope with the conjugated antibody to form the radiolabeled antibody. A radioisotope may be chelated by the conjugated antibody at any time following conjugation.

According to certain aspects of the present invention, the radiolabeled targeting agent may be relatively stable. For example, greater than 75% of the targeting agent labelled with $^{225}$Ac- or $^{131}$I-may remain intact after storage for 24 hours at 4° C. According to certain aspects of the present invention, the radiolabeled targeting agent may be prepared as a composition by the methods disclosed in the International Patent Application Publication No. WO2016/187514. Moreover, the radiolabeled targeting agent may be administered by methods disclosed in the same publication.

According to certain aspects of the present invention, the radiolabeled targeting agent may exhibit essentially the same immunoreactivity to the antigen as a control targeting agent, wherein the control targeting agent comprises an un-labeled targeting agent against the same epitope of the antigen (i.e., CD33) as the $^{225}$Ac- or $^{131}$I-labelled targeting agent.

According to certain aspects of the present invention, the radiolabeled anti-CD33 targeting agent is radiolabeled HuM195 (lintuzumab). Radiolabeled antibodies envisioned in this invention include, without limitation, $^{131}$I-HuM195, $^{125}$I-HuM195, $^{123}$I-HuM195, $^{90}$Y-HuM195, $^{177}$Lu-HuM195, $^{186}$Re-HuM195, $^{188}$Re-HuM195, $^{89}$Sr-HuM195, $^{153}$Sm-HuM195, $^{32}$P-HuM195, $^{225}$Ac-HuM195, $^{213}$Bi-HuM195, $^{213}$Po-HuM195, $^{211}$At-HuM195, $^{212}$Bi-HuM195, $^{213}$Bi-HuM195, $^{223}$Ra-HuM195, $^{227}$Th-HuM195, $^{149}$Tb-HuM195, $^{131}$I-HuM195, $^{137}$Cs-HuM195, $^{212}$Pb-HuM195 and $^{13}$Pd-HuM195. Preferably, the radiolabeled anti-CD33 antibody is $^{131}$I-HuM195 or $^{225}$Ac-HuM195.

According to certain aspects of the present invention, the targeting agent may be labelled with $^{225}$Ac, and may be at least 5-fold more effective at causing cell death of lymphoblast or myeloma cells than a control monoclonal antibody, wherein the control targeting agent comprises an un-labeled targeting agent against the same epitope of the antigen as the $^{225}$Ac labelled targeting agent. For example, a $^{225}$Ac labelled monoclonal antibody may be at least 10-fold more effective, at least 20-fold more effective, at least 50-fold more effective, or at least 100-fold more effective at causing cell death of lymphoblast or myeloma cells than the control monoclonal antibody.

According to certain aspects of the present invention, the methods may comprise administration of labeled and un-labelled (e.g., "naked") fractions of the anti-CD33 targeting agent, such as an antibody, antibody fragment, etc. For example, the un-labeled fraction may comprise the same antibody against the same epitope as the labeled fraction. In this way, the total radioactivity of the antibody may be varied or may be held constant while the overall antibody protein concentration may held constant or may be varied, respectively. For example, the total protein concentration of un-labelled antibody fraction administered may vary depending on the exact nature of the disease to be treated, age and weight of the patient, identity of the monoclonal antibody, and the label (e.g., radionuclide) selected for labeling of the monoclonal antibody.

According to certain aspects of the present invention, the effective amount of $^{131}$I-HuM195 is from 10 mCi to 200 mCi. Examples of effective amounts include, without limitation, from 50 mCi to 100 mCi, from 50 mCi to 150 mCi, from 50 mCi to 200 mCi, from 60 mCi to 140 mCi, from 70 mCi to 130 mCi, from 80 mCi to 120 mCi, from 90 mCi to 110 mCi, from 100 mCi to 150 mCi, 50 mCi, 60 mCi, 70 mCi, 80 mCi, 90 mCi, 100 mCi, 110 mCi, 120 mCi, 130 mCi, 140 mCi, 150 mCi, or 200 mCi. According to certain aspects of this method, the effective amount of $^{131}$I-HuM195 is from 200 mCi to 1200 mCi. Examples of effective amounts include, without limitation, from 200 mCi to 300 mCi, from 200 mCi to 400 mCi, from 200 mCi to 500 mCi, from 200 mCi to 600 mCi, from 200 mCi to 700 mCi, from 200 mCi to 800 mCi, from 200 mCi to 900 mCi, from 200 mCi to 1000 mCi, from 200 mCi to 1100 mCi, from 300 mCi to 1200 mCi, from 400 mCi to 1200 mCi, from 500 mCi to 1200 mCi, from 600 mCi to 1200 mCi, from 700 mCi to 1200 mCi, from 800 mCi to 1200 mCi, from 900 mCi to 1200 mCi, from 1000 mCi to 1200 mCi, 50 mCi, 100 mCi, 150 mCi, 200 mCi, 300 mCi, 400 mCi, 500 mCi, 600 mCi, 700 mCi, 800 mCi, 900 mCi, 1000 mCi, or 1100 mCi.

According to certain aspects of the present invention, the effective amount of $^{225}$Ac-HuM195 is below, for example, 5.0 µCi/kg (i.e., where the amount of $^{225}$Ac-labeled antibody administered to the subject delivers a radiation dose of below 5.0 µCi per kilogram of subject's body weight). According to certain aspects, the effective amount of $^{225}$Ac-HuM195 is below 4.5 µCi/kg, 4.0 µCi/kg, 3.5 µCi/kg, 3.0 µCi/kg, 2.5 µCi/kg, 2.0 µCi/kg, 1.5 µCi/kg, 1.0 µCi/kg, 0.9 µCi/kg, 0.8 µCi/kg, 0.7 µCi/kg, 0.6 µCi/kg, 0.5 µCi/kg, 0.4 µCi/kg, 0.3 µCi/kg, 0.2 µCi/kg, 0.1 µCi/kg or 0.05 µCi/kg. According to certain aspects, the effective amount of $^{225}$Ac-HuM195 is from 0.05 µCi/kg to 0.1 µCi/kg, from 0.1 µCi/kg to 0.2 µCi/kg, from 0.2 µCi/kg to 0.3 µCi/kg, from 0.3 µCi/kg to 0.4 µCi/kg, from 0.4 µCi/kg to 0.5 µCi/kg, from 0.5 µCi/kg to 0.6 µCi/kg, from 0.6 µCi/kg to 0.7 µCi/kg, from 0.7 µCi/kg to 0.8 µCi/kg, from 0.8 µCi/kg to 0.9 µCi/kg, from 0.9 µCi/kg to 1.0 µCi/kg, from 1.0 µCi/kg to 1.5 µCi/kg, from 1.5 µCi/kg to 2.0 µCi/kg, from 2.0 µCi/kg to 2.5 µCi/kg, from 2.5 µCi/kg to 3.0 µCi/kg, from 3.0 µCi/kg to 3.5 µCi/kg, from 3.5 µCi/kg to 4.0 µCi/kg, from 4.0 µCi/kg to 4.5 µCi/kg, or from 4.5 µCi/kg to 5.0 µCi/kg. According to certain aspects, the effective amount of $^{225}$Ac-HuM195 and/or $^{225}$Ac-Dara is 0.05 µCi/kg, 0.1 µCi/kg, 0.2 µCi/kg, 0.3 µCi/kg, 0.4 µCi/kg, 0.5 µCi/kg, 0.6 µCi/kg, 0.7 µCi/kg, 0.8 µCi/kg, 0.9 µCi/kg, 1.0 µCi/kg, 1.5 µCi/kg, 2.0 µCi/kg, 2.5 µCi/kg, 3.0 µCi/kg, 3.5 µCi/kg, 4.0 µCi/kg or 4.5 µCi/kg.

According to certain aspects of the present invention, the $^{225}$Ac-labeled anti-CD33 antibody may be administered as one or more doses according to any of the dosing schedules listed herein until the subject has received a cumulative radiation dose of 1 µCi/kg, 2 µCi/kg, 3 µCi/kg, 4 µCi/kg, 5 µCi/kg, 6 µCi/kg, 7 µCi/kg, 8 µCi/kg, 9 µCi/kg, or 10 µCi/kg of patient weight.

According to certain aspects of the present invention, an effective amount of the anti-CD33 antibody may comprises a dose of 0.5 to 4 uCi/kg of subject's body weight. In general, the effective amount of the anti-CD33 antibody comprises a dose of less than 16 mg/kg body weight, such as from 0.01 mg/kg to 5 mg/kg.

According to certain aspects of the present invention, the effective amount of the anti-CD33 antibody is a maximum tolerated dose (MTD) of the anti-CD33 antibody.

According to certain aspects of the methods of the present invention, when more than one antibody is administered, the antibodies may be administered at the same time. As such, according to certain aspects of the present invention, the antibodies may be provided in a single composition. Alternatively, the two antibodies may be administered sequentially. As such, the anti-CD33 targeting agent may be administered before the second antibody, after the second antibody, or both before and after the second antibody. Moreover, the second antibody may be administered before the anti-CD33 targeting agent, after the anti-CD33 targeting agent, or both before and after the anti-CD33 targeting agent.

According to certain aspects of the methods of the present invention, the anti-CD33 targeting agent may be administered according to a dosing schedule selected from the group consisting of one every 7, 10, 12, 14, 20, 24, 28, 35, and 42 days throughout a treatment period, wherein the treatment period includes at least two doses.

According to certain aspects of the present invention, the anti-CD33 targeting agent may be administered according to a dose schedule that includes 2 doses, such as on days 1 and 5, 6, 7, 8, 9, or 10 of a treatment period, or days 1 and 8 of a treatment period.

The methods of the present invention, which include administration of monospecific and/or multi-specific immunological agents, may further comprise administering one or more further therapeutic agents. The additional therapeutic agents may be relevant for the disease or condition to be treated. Such administration may be simultaneous, separate or sequential with the administration of the effective amount of each antibody agent detailed herein. For simultaneous administration, the agents may be administered as one composition (antibody and therapeutic agent) or as separate compositions, as appropriate.

Exemplary additional therapeutic agents include at least chemotherapeutic agents, anti-inflammatory agents, immunosuppressive agents, immunomodulatory agents, or a combination thereof. Moreover, the one or more further therapeutic agents may comprise an antimyeloma agent, such as dexamethasone, doxorubicin, bortezomib, lenalidomide, prednisone, carmustine, etoposide, cisplatin, vincristine, cyclophosphamide, and thalidomide.

According to certain aspects of the present invention, the methods may further comprise administration of a cytokine such as granulocyte colony-stimulating factor (GCSF) after administration of the anti-CD33 targeting agent. The GCSF may be administered, for example, 7, 8, 9, 10, or 11 days after administration of the anti-CD33 targeting agent.

According to certain aspects of the present invention, the methods may further comprise administration of a chemotherapeutic agent such as, for example, fludarabine, busulfan, cyclophospharnide, or melphalan, after administration of the anti-CD33 targeting agent. The chemotherapeutic agent may be administered, for example, 7, 8, 9, 10, or 11 days after administration of the anti-CD33 targeting agent. An exemplary method of the present invention includes administration of the anti-CD33 targeting agent on day 0, and the chemotherapeutic agent on days 7, 8, 9, 10, and 11. The BMT or HSCT may then be performed in day 12. Exemplary doses of the chemotherapeutic agents include, for example, 10 to 40 mg/day, such as 20 or 30 mg/day.

The therapeutic agents may be administered according to any standard dose regime known in the field. For example, therapeutic agents may be administered at concentrations in the range of 1 to 500 mg/m$^2$, the amounts being calculated as a function of patient surface area (m$^2$).

The methods of the present invention may further comprise transplanting autologous or allogeneic stem cells to the subject after administration of the anti-CD33 targeting agent. When the anti-CD33 targeting agent is labelled with a radionuclide, the stem cells may be transplanted at a time after administration of the anti-CD33 targeting agent when a radiation dose from the anti-CD33 targeting agent is not harmful to the transplanted cells, such as 8 to 20 days after the administration of the anti-CD33 targeting agent, or even 10 to 16 days after administration of the anti-CD33 targeting agent, or 8, 9, 10, 11, 12, 13, 14, 15, or 16 days after administration of the anti-CD33 targeting agent.

Transplantation of stem cells may include infusion of hematopoietic stem cells derived from any appropriate source of stem cells in the body. The stem cells may be derived, for example, from bone marrow, from the peripheral circulation following mobilization from the bone marrow, or from fetal sources such as fetal tissue, fetal circulation and umbilical cord blood. Bone marrow transplantation is considered herein to be simply one form of stem cell transplantation. Mobilization of stem cells from the bone marrow can be accomplished, for example, by treatment of the donor with granulocyte colony stimulating factor (G-CSF) or other appropriate factors (e.g., IL-8) that induce movement of stem cells from the bone marrow into the peripheral circulation. Following mobilization, the stem cells can be collected from peripheral blood by any appropriate cell apheresis technique.

Infusion of the hematopoietic stem cells may result in complete and permanent engraftment (i.e., 100% donor hematopoietic cells), or may result in partial and transient engraftment, provided the donor cells persist sufficiently long to permit performance of allogeneic cell therapy as described herein. Thus, the term "stem cell transplantation" covers stem cell infusion into a patient resulting in either complete or partial engraftment as described above.

Allogeneic lymphocytes infused into a patient need not be infused as a purified T-cell preparation. Although it is possible to infuse a relatively pure T-cell preparation, the cells may be infused in the form of a peripheral blood mononuclear cell (PBMC) preparation. In appropriate circumstances it is even possible to administer allogeneic lymphocytes to the patient by simply providing whole blood.

Administration of the anti-CD33 targeting agents such as antibodies of the present invention, in addition to other therapeutic agents, may be provided in a number of ways depending upon whether local or systemic treatment is desired and upon the area to be treated. Administration may be intratracheal, intranasal, epidermal and transdermal, oral or parenteral. Parenteral administration includes intravenous, intra-arterial, subcutaneous, intraperitoneal or intramuscular injection or infusion; or intracranial, e.g., intrathecal or intraventricular, administration. In some embodiments a slow release preparation comprising the monoclonal antibodies and/or other therapeutic agents may be administered. The various agents may be administered as a single treatment or in a series of treatments that continue as needed and for a duration of time that causes one or more symptoms of the cancer to be reduced or ameliorated, or that achieves another desired effect.

The dose(s) may vary, for example, depending upon the identity, size, and condition of the subject, further depending upon the route by which the composition is to be administered and the desired effect. Appropriate doses of a therapeutic agent depend upon the potency with respect to the expression or activity to be modulated. The therapeutic agents can be administered to an animal (e.g., a human) at a relatively low dose at first, with the dose subsequently increased until an appropriate response is obtained.

The proliferative disorder may be one or more solid cancers. The mutational status of p53 has been shown to predict poor outcomes in multiple types of human tumors (e.g., breast cancer), and certain mutants of p53 associate with an even worse prognosis. Mutant p53 has also been demonstrated to lead to increased invasion, migration and metastasis in preclinical breast cancer models. Thus, the present invention contemplates treatment methods for solids cancers.

EXAMPLES

Example 1: Anti-CD33 Targeting Agent Specificity and Stability

Lintuzumab conjugated with Actinium-225 ($Ac^{225}$) was tested for cytotoxicity against specific cell types which express CD33. For example, suspensions of HL60 (leukemia cells) were incubated with various doses of radiolabeled lintuzumab (lintuzumab-$Ac^{225}$), and the dose at which 50% of the cells were killed ($LD_{50}$) was found to be 8 µCi per mL of cell suspension.

In studies to access the reactivity of the radiolabeled lintuzumab with peripheral blood and bone marrow cells from nonhuman primate and human frozen tissues, the radiolabeled lintuzumab showed reactivity with mononuclear cells only, demonstrating specificity. Moreover, in studies to determine the stability of the radiolabel on the antibody, 10 normal mice (8 week old Balb/c female mice from Taconic, Germantown, New York) were injected in the tail with 300 nCi radiolabeled lintuzumab (in 0.12 ml). Serum samples taken over a 5 day period showed that the Actinium-225 remained bound to the lintuzumab, demonstrating the stability of the radiolabel on the antibody in vivo. Moreover, similar studies in male monkeys (*Macaca fascicularis*, 4-6 kg) receiving a dose of 0.76 uCi/kg lintuzumab-Ac225 showed a blood half-life of approximately 12 days.

A maximum tolerated dose (MTD) of a single injection of the radiolabeled lintuzumab was determined to be 3 uCi/kg patient weight. As a split dose (e.g., 2 equal doses administered 4-7 days apart), the MTD was determined to be 2 uCi/kg per dose, or 4 uCi/kg total. This data was determined by injections into patients with relapsed/refractory AML: 21 patients were injected with increasing doses of the radiolabeled lintuzumab—0.5 uCi/kg to 4 uCi/kg. Determination of MTD was based on the severity of the adverse effects observed at each dose level. Anti-leukemic effects included elimination of peripheral blood blasts in 13 of 19 evaluable patients. Twelve of 18 patients who were evaluable at 4 weeks following treatment had reductions in bone marrow blasts, including nine with reductions ≥50%. Three patients treated with 1 uCi/kg, 3 uCi/kg and 4 uCi/kg respectively had ≤5% blasts after therapy.

Example 2: Anti-CD33 Targeting Agent Human Maximal Tolerated Dose and Efficacy

A Phase I trial will be used to determine the MTD of fractionated doses of lintuzumab-$Ac^{225}$ followed by Granulocyte Colony Stimulating factor (GCSF) support in each cycle. A cycle in general is approximately 42 days. A cycle starts with administration of a fractionated dose of Lintuzumab-$Ac^{225}$ on Day 1 followed by the administration of GCSF on Day 9 and continuing GCSF per appropriate dosing instructions until absolute neutrophil count (ANC) is greater than 1,000, which is expected to occur within 5-10 days. On Days 14, 21, 28, 35 and 42 peripheral blood will be assessed for paraprotein burden. A bone marrow aspirate will be performed to assess plasmocyte infiltration on Day 42. If a response is a partial response or better but less than a complete response on Day 42, and the patient remains otherwise eligible, the patient will be re-dosed in a new cycle at the same dose level no sooner than 60 days after Day 1 of the first cycle. In absence of dose limiting toxicities, cycles will continue using the above described algorithm until the patient has received a cumulative dose of 4 µCi/kg of lintuzumab-Ac$^{225}$.

Example 3: Treatment of AML with Anti-CD33 Targeting Agent

Patients with AML are being enrolled into the phase I clinical trial. Eligible patients are those between 60 and 75 years of age who are considered "unfit" for the administration of standard cytotoxic chemotherapy treatments, and patients 75 and older who are all eligible. The MTD for this patient subset is investigated in the range of 1 to 4 uCi/kg patient weight. For example, patients received single-agent lintuzumab-Ac-$^{225}$ at a dose of 2 uCi/kg patient body weight administered in an outpatient setting on days 1 and 8 of the study. The evaluation of p53 mutations was recently added to the molecular testing for patients in this study. From other studies, p53 mutations are known to be uncommon in patients with AML (and patients with p53 mutations have a poor prognosis compared to those without p53 mutations (Prokocimer, et al., Blood 2017). Alphaparticle therapy is not dependent on the presence of p53, since in vitro lintuzumab-Ac-$^{225}$ is effective in killing HL-60 cells, which lack p53 genes.

Early evidence from the phase I study indicates that lintuzumab-Ac-$^{225}$ can be effective in the treatment of patients whose AML has p53 mutations present. One patient with documented p53 mutation at baseline responded to lintuzumab-Ac-$^{225}$ therapy with a remission. Patient 003-005 was a 71 year old female patient with a treatment-related AML. The patient had previously received treatment for Non-Hodgkins' lymphoma consisting of R-EPOCH chemotherapy (Rituxan, etoposide, prednisone, oncovin, cyclophosphamide, and hydroxydaunorubicin). She then developed AML and at baseline was found to have a p53 mutation in the DNA binding region of the molecule (c613T>G; pTyr205Asp). At baseline the patient had 66% AML blasts in the bone marrow and adverse cytogenetic findings (hyperdiploid, 3-4 extra chromosomes including trisomy 8 and trisomy 9). At baseline the patient had an ECOG Performance Status of 3 (capable of only limited selfcare, confined to bed for chair for more than 50% of waking hours). The bone marrow examination on study day 55 documented 1% AML blasts, a 99% decrease in AML blasts. This case demonstrates that lintuzumab-Ac-$^{225}$ treatment can lead to remissions in AML with p53 mutations.

The following aspects are disclosed in this application:

Aspect 1. A method of treating a hematologic malignancy in a subject having a complex karyotype, the method comprising: administering to the subject an effective amount of an anti-CD33 targeting agent.

Aspect 2. The method of aspect 1, wherein the hematologic malignancy comprises myelodysplastic syndrome (MDS), multiple myeloma (MM), acute myeloid leukemia (AML), myeloproliferative neoplasm, or a combination thereof.

Aspect 3. The method of aspects 1 or 2, wherein the hematologic malignancy comprises myelodysplastic syndrome (MDS).

Aspect 4. The method of aspect 2 or 3, wherein the MDS is categorized as a poor or a very poor cytogenetic prognostic subgroup by IPSS-R.

Aspect 5. The method according to any one of aspects 1 to 4, wherein the anti-CD33 targeting agent comprises a radiolabel selected from $^{131}$I, $^{125}$I, $^{123}$I, $^{90}$Y, $^{177}$Lu, $^{186}$Re, $^{188}$Re, $^{89}$Sr, $^{153}$Sm, $^{32}$P, $^{225}$Ac, $^{213}$Bi, $^{213}$Po, $^{211}$At, $^{212}$Bi, $^{213}$Bi, $^{223}$Ra, $^{227}$Th, $^{149}$Tb, $^{137}$Cs, $^{212}$Pb or $^{103}$Pd, or a combination thereof.

Aspect 6. The method according to any one of aspects 1 to 5, wherein the anti-CD33 targeting agent comprises a humanized antibody against CD33.

Aspect 7. The method according to any one of aspects 1 to 6, wherein the anti-CD33 targeting agent comprises lintuzumab, gemtuzumab, and vadastuximab.

Aspect 8. The method according to any one of aspects 1 to 7, wherein the anti-CD33 targeting agent is $^{131}$I- or $^{225}$Ac-labelled and the effective amount of the anti-CD33 targeting agent comprises a dose of 0.1 to 10 uCi/kg body weight of the subject, or 0.2 to 8 uCi/kg body weight of the subject, or 0.5 to 4 uCi/kg subject body weight.

Aspect 9. The method according to any one of aspects 1 to 8, wherein the effective amount of the anti-CD33 targeting agent comprises a dose of less than 16 mg/kg body weight of the subject, less than 10 mg/kg body weight of the subject, or less than 6 mg/kg body weight of the subject.

Aspect 10. The method according to any one of aspects 1 to 9, wherein the anti-CD33 targeting agent is administered according to a dosing schedule selected from the group consisting of once every 7, 10, 12, 14, 20, 24, 28, 36, and 42 days throughout a treatment period, wherein the treatment period includes at least two doses.

Aspect 11. The method according to any one of aspects 1 to 10, wherein the effective amount of the anti-CD33 targeting agent is an amount sufficient to induce myeloconditioning, or an amount sufficient to induce myeloablation.

Aspect 12. The method according to any one of aspects 1 to 11, further comprising: transplanting allogeneic stem cells to the subject after administration of the anti-CD33 targeting agent.

Aspect 13. The method of aspect 12, wherein the transplantation is performed 8 to 20 days after administration of the anti-CD33 targeting agent, or wherein the transplantation is performed 10 to 16 days after the administration of the anti-CD33 targeting agent.

Aspect 14. The method according to any one of aspects 1 to 13, further comprising: administering to the subject a second therapeutic agent, wherein administration of the second therapeutic agent is simultaneous or sequential with administration of the anti-CD33 targeting agent.

Aspect 15. The method of aspect 14, wherein the second therapeutic agent comprises an anti-CD45 targeting agent at least partially labelled with a radiolabel.

Aspect 16. The method of aspect 15, wherein the anti-CD45 targeting agent is $^{131}$I-BC8 administered at from 10 mCi to 1,200 mCi, or from 10 mCi to 200 mCi, or from 200 mCi to 400 mCi, or from 400 mCi to 1,200 mCi; or wherein the anti-CD45 targeting agent is $^{225}$Ac-BC8 administered at from 0.1 µCi/kg to 5.0 µCi/kg subject weight, or from 0.1 µCi/kg to 1.0 µCi/kg subject weight, or from 1.0 µCi/kg to 3.0 µCi/kg subject weight, or from 3.0 µCi/kg to 5.0 µCi/kg subject weight.

Aspect 17. The method according to any one of aspects 13 to 16, wherein the second therapeutic agent comprises a chemotherapeutic agent, an anti-inflammatory agent, an immunosuppressive, an immunomodulatory agent, an anti-myeloma agent, or a combination thereof.

Aspect 18. The method according to any one of aspects 13 to 17, wherein the second therapeutic agent comprises granulocyte colony-stimulating factor.

Aspect 19. The method according to any one of aspects 13 to 17, wherein the second therapeutic agent is a chemotherapeutic agent administered 7, 8, 9, 10, and/or 11 days after the anti-CD33 targeting agent, wherein the chemotherapeutic agent is selected from fludarabine, busulfan, cyclophosphamide, melphalan, or a combination thereof.

Aspect 20. The method according to any one of aspects 1 to 19, wherein the anti-CD33 targeting agent is a multi-specific antibody, wherein the multi-specific antibody comprises: a first target recognition component which specifically binds to an epitope of CD33, and a second target recognition component which specifically binds to a different epitope of CD33 than the first target recognition component, or an epitope of a different antigen.

Aspect 21. A method for treating a subject having a myelodysplastic syndrome, the method comprising: determining if the subject has a complex karyotype; and if the subject has the complex karyotype, proceeding with administration of an effective amount of an anti-CD33 targeting agent, wherein anti-CD33 targeting agent comprises lintuzumab, gemtuzumab, and vadastuximab at least partially labelled with a radiolabel selected from $^{131}$I, $^{125}$I, $^{123}$I, $^{90}$Y, $^{177}$Lu, $^{186}$Re, $^{188}$Re, $^{89}$Sr, $^{153}$Sm, $^{32}$P, $^{225}$Ac, $^{213}$Bi, $^{213}$Po, $^{211}$At, $^{212}$Bi, $^{213}$Bi, $^{223}$Ra, $^{227}$Th, $^{149}$Tb, $^{137}$Cs, $^{212}$Pb or $^{103}$Pd, or a combination thereof.

Aspect 22. The method of aspect 21, wherein the anti-CD33 targeting agent comprises $^{131}$I- or $^{225}$Ac-labelled lintuzumab, and the effective amount of the anti-CD33 targeting agent comprises a dose of 0.1 to 10 uCi/kg body weight of the subject, or 0.2 to 8 uCi/kg body weight of the subject, or 0.5 to 4 uCi/kg subject body weight.

Aspect 23. The method of aspect 21 or 22, further comprising: transplanting allogeneic stem cells to the subject after administration of the anti-CD33 targeting agent, wherein the effective amount of the anti-CD33 targeting agent induced myeloablation, and wherein the transplantation is performed 8 to 20 days after the administration of the anti-CD33 targeting agent, or wherein the transplantation is performed 10 to 16 days after the administration of the anti-CD33 targeting agent.

Aspect 24. The method according to any one of aspects 21 to 23, wherein the anti-CD33 targeting agent is administered as a single bolus or infusion in a subject specific dose.

Aspect 25. The method of aspect 24, wherein the subject specific dose comprises the $^{131}$I- or $^{225}$Ac-labelled lintuzumab at 0.5 to 4 uCi/kg subject body weight, and less than 6 mg/kg body weight of the subject.

What is claimed is:

1. A method of treating a hematologic malignancy in a subject comprising administering to the subject an effective amount of an anti-CD33 targeting agent, wherein the subject has a complex karyotype or a p53 mutation,
   wherein the anti-CD33 targeting agent comprises a radiolabel selected from the group consisting of $^{131}$I, $^{125}$I, $^{123}$I, $^{90}$Y, $^{177}$Lu, $^{186}$Re, $^{188}$Re, $^{89}$Sr, $^{153}$Sm, $^{32}$P, $^{225}$Ac, $^{213}$Bi, 213Po, 211At, 212Bi, $^{213}$Bi, $^{223}$Ra, $^{227}$Th, $^{149}$Tb, $^{137}$Cs, $^{212}$Pb, and $^{103}$Pd, and
   wherein the hematologic malignancy comprises myelodysplastic syndrome (MDS), multiple myeloma (MM), acute myeloid leukemia (AML), myeloproliferative neoplasm, or a combination thereof, and
   wherein the anti-CD33 targeting agent comprises lintuzumab, gemtuzumab, or vadastuximab;
   and wherein the effective amount of the anti-CD33 targeting agent is an amount sufficient to induce myeloconditioning, or an amount sufficient to induce myeloablation.

2. The method of claim 1, wherein the hematologic malignancy comprises myelodysplastic syndrome (MDS) and the MDS is categorized as a poor or a very poor cytogenetic prognostic subgroup by IPSS-R.

3. The method of claim 1, further comprising:
   obtaining a sample of cells from the subject wherein the cells are cancer cells, precancer cells, or cells from a tumor;
   assaying the cells for the presence of a mutated p53 gene or a mutant form of p53 protein; and
   if the cells have the mutated p53 gene or the mutant form of the p53 protein, proceeding with administration of the effective amount of the anti-CD33 targeting agent.

4. The method of claim 1, wherein the anti-CD33 targeting agent is administered as a single bolus or infusion in a subject specific dose, wherein the anti-CD33 targeting agent is $^{131}$I- or $^{225}$Ac-labelled and the subject specific dose comprises a radiation dose of 0.1 to 10 uCi/kg body weight of the subject and a total protein dose of between 0.2 to 0.6 mg/kg body weight of the subject.

5. The method of claim 4, wherein the anti-CD33 targeting agent is administered according to a dosing schedule selected from the group consisting of once every 7, 10, 12, 14, 20, 24, 28, 36, and 42 days throughout a treatment period, wherein the treatment period includes at least two doses.

6. The method of claim 1, further comprising:
   transplanting allogeneic stem cells to the subject after administration of the anti-CD33 targeting agent, wherein the transplantation is performed 8 to 20 days after administration of the anti-CD33 targeting agent.

7. The method of claim 1, further comprising:
   administering to the subject a second therapeutic agent, wherein administration of the second therapeutic agent is simultaneous or sequential with administration of the anti-CD33 targeting agent.

8. The method of claim 7, wherein the second therapeutic agent comprises an anti-CD45 targeting agent, wherein the anti-CD45 targeting agent is $^{131}$I-BC8 administered at from 10 mCi to 1,200 mCi, or wherein the anti-CD45 targeting agent is $^{225}$Ac-BC8 administered at from 0.1 µCi/kg to 5.0 µCi/kg subject weight.

9. The method of claim 7, wherein the second therapeutic agent comprises a chemotherapeutic agent, an anti-inflammatory agent, an immunosuppressive, an immunomodulatory agent, an antimyeloma agent, or a combination thereof.

10. The method of claim 7, wherein the second therapeutic agent comprises granulocyte colony-stimulating factor.

11. The method of claim 7, wherein the second therapeutic agent is a chemotherapeutic agent administered 7, 8, 9, 10, or 11 days after the anti-CD33 targeting agent, wherein the chemotherapeutic agent is selected from fludarabine, busulfan, cyclophosphamide, melphalan, or a combination thereof.

12. The method of claim 1, wherein the anti-CD33 targeting agent is a multi-specific antibody, wherein the multi-specific antibody comprises:
   a first target recognition component which specifically binds to an epitope of CD33, and a second target recognition component which specifically binds to a different epitope of CD33 than the first target recognition component, or an epitope of a different antigen.

13. A method for treating a subject having a myelodysplastic syndrome, the method comprising:
   determining if the subject has a complex karyotype as indicated by the myelodysplastic syndrome categorized as a poor or very poor cytogenetic prognostic subgroup in the IPSS-R; and
   if the subject has the complex karyotype, proceeding with administration of an effective amount of an anti-CD33 targeting agent,
   wherein the anti-CD33 targeting agent is $^{131}$I-or $^{225}$Ac-labelled and is administered as a single bolus or infusion in a subject specific dose comprising a radiation dose of 0.1 to 10 uCi/kg body weight of the subject, and a total protein dose of less than 16 mg/kg body weight of the subject, and
   wherein the anti-CD33 targeting agent comprises lintuzumab.

14. The method of claim 13, wherein the anti-CD33 targeting agent is $^{225}$Ac-labelled lintuzumab and the subject specific dose comprises the radiation dose of 0.5 to 4 uCi/kg subject body weight, and the total protein dose of less than 6 mg/kg body weight of the subject.

15. The method of claim 13, wherein the effective amount of the anti-CD33 targeting agent induces myeloablation, and the method further comprises:
   transplanting allogeneic stem cells to the subject after administration of the anti-CD33 targeting agent,
   wherein the transplantation is performed 8 to 20 days after the administration of the anti-CD33 targeting agent.

16. A method for treating a subject having a myelodysplastic syndrome, the method comprising:
   determining if the subject has one or both of a mutated p53 gene or a mutant form of p53 protein; and
   if the subject has one or both of the mutated p53 gene or the mutant form of the p53 protein, proceeding with administration of an effective amount of an anti-CD33 targeting agent,
   wherein the anti-CD33 targeting agent is $^{131}$I-or $^{225}$Ac-labelled and is administered as a single bolus or infusion in a subject specific dose comprising a radiation dose of 0.1 to 10 uCi/kg body weight of the subject, and a total protein dose of less than 16 mg/kg body weight of the subject, and
   wherein the anti-CD33 targeting agent comprises lintuzumab.

17. The method of claim 16, wherein the anti-CD33 targeting agent is $^{225}$Ac-labelled lintuzumab and the subject specific dose comprises the radiation dose of 0.5 to 4 uCi/kg subject body weight, and the total protein dose of less than 6 mg/kg body weight of the subject.

18. The method of claim 16, wherein the effective amount of the anti-CD33 targeting agent induces myeloablation, and the method further comprises:
   transplanting allogeneic stem cells to the subject after administration of the anti-CD33 targeting agent,
   wherein the transplantation is performed 8 to 20 days after the administration of the anti-CD33 targeting agent.

* * * * *